United States Patent
McHardy et al.

(10) Patent No.: US 7,473,787 B2
(45) Date of Patent: Jan. 6, 2009

(54) BICYCLIC [3.1.0] DERIVATIVES AS GLYCINE TRANSPORTER INHIBITORS

(75) Inventors: Stanton McHardy, Coventry, RI (US); John A. Lowe, Stonington, CT (US)

(73) Assignee: Pfizer Inc, New York, NY (US)

( * ) Notice: Subject to any disclaimer, the term of this patent is extended or adjusted under 35 U.S.C. 154(b) by 372 days.

(21) Appl. No.: 10/964,931

(22) Filed: Oct. 14, 2004

(65) Prior Publication Data
US 2005/0096375 A1  May 5, 2005

Related U.S. Application Data

(60) Provisional application No. 60/510,846, filed on Oct. 14, 2003.

(51) Int. Cl.
*C07D 209/52* (2006.01)
(52) U.S. Cl. ..................................... 548/515
(58) Field of Classification Search ................ 544/139
See application file for complete search history.

(56) References Cited

U.S. PATENT DOCUMENTS 6,897,230 B2 * 5/2005 Fukuda et al. ............... 514/376

FOREIGN PATENT DOCUMENTS

| WO | WO 03/037865 | 5/2003 |
|----|--------------|--------|
| WO | WO 2005/115992 | 12/2005 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the internet, URL; http:www.cnn.com/2003/HEALTH/conditions/09/24/alzheimers.drug.ap/index.html>.*
Cognitive disorder [online], [retrieved on Sep. 1, 2006]. Retrieved from the Internet, URL; http://en.wikipedia.org/wiki/Category:Cognitive_disorders>.*
Dementia [online], [retrieved on May 24, 2007]. Retrieved from the Internet, URL; http://en.wikipedia.org/wiki/Dementia>.*

* cited by examiner

*Primary Examiner*—Kamal A Saeed
*Assistant Examiner*—Shawquia Young
(74) *Attorney, Agent, or Firm*—Steve T. Zelson; Garth Butterfield; Sandra Kim

(57) ABSTRACT

The present invention relates to a series of substituted bicyclic [3.1.0]amines of the Formula I:

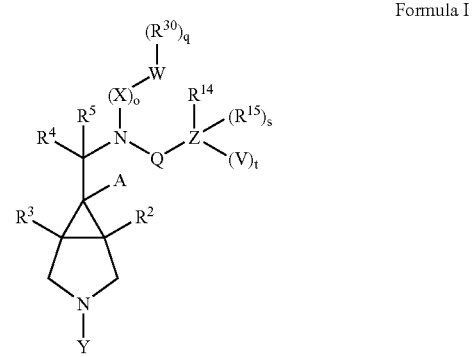

Formula I wherein A, B, D, Q, V, W, X, Y, Z, $R^2$, $R^3$, $R^4$, $R^5$, $R^{14}$, $R^{15}$, $R^{30}$. o, p, s,t and q are as defined in the specification, their pharmaceutically acceptable salts, pharmaceutical compositions thereof, and their use for the enhancement of cognition and the treatment of the positive and negative symptoms of schizophrenia and other psychoses in mammals, including humans.

4 Claims, No Drawings

BICYCLIC [3.1.0] DERIVATIVES AS GLYCINE TRANSPORTER INHIBITORS

CROSS REFERENCE TO RELATED APPLICATIONS

This application claims the benefit of U.S. Ser. No. 60/510,846, filed on Oct. 14, 2003.

BACKGROUND OF THE INVENTION

The present invention relates to bicyclic[3.1.0]amines and to pharmaceutical compositions containing them and to their use in the treatment of central nervous system disorders, cognitive disorders, schizophrenia, dementia and other disorders in mammals, including humans. These compounds exhibit activity as inhibitors of the glycine type-1 transporter.

Schizophrenia, a progressive neurological disease, is manifested in its early stages as thought disorders such as hallucinations, paranoid delusions, and bizarre thought patterns, collectively known as positive symptoms. These easily recognizable symptoms gave the disease the historical name "madness". As the disease progresses, negative symptoms, such as social withdrawal and anhedonia, and cognitive symptoms such as dementia become more apparent. Only about one-third of schizophrenic patients can be treated successfully and returned to society, while the remainder is generally institutionalized. The burden on society of this devastating illness and the toll it takes on family members of affected patients make it one of the most costly of all CNS diseases.

Pharmacological treatment for schizophrenia has traditionally involved blockade of the dopamine system, which is thought to be responsible for its positive symptoms. Such treatment, however, ignores the negative and cognitive aspects of the disease. Another neurotransmitter system believed to play a role in schizophrenia is the glutamate system, the major excitatory transmitter system in the brain. This hypothesis is based on the observation that blockade of the glutamate system by compounds such as PCP ("angel dust") can replicate many of the symptoms of schizophrenia, including its positive, negative, and cognitive aspects. If schizophrenia involves a deficit of glutamatergic transmission, augmentation of the glutamate system, and specifically the NMDA receptor, can be beneficial. While glutamate is the principle agonist at NMDA receptors, glycine is required as a co-agonist to set the "tone" of the receptor for its response to glutamate. Enhancing this "tone" by increasing the effect of glycine would augment NMDA neurotransmission, and provide potential benefit in the treatment of schizophrenia.

A specific mechanism for augmenting the glycinergic "tone" of the NMDA receptor was disclosed recently by Bergeron, et al. (*Proc. Natl. Acad. Sci. USA,* 95, 15730, (1998)), which is hereby incorporated by reference. This group showed that a specific and potent inhibitor of the glycine type-1 transporter (GlyT1) responsible for removing glycine from the synapse at the NMDA receptor, termed NFPS (WO 97/45115), could enhance NMDA receptor function. For example, NFPS increased the postsynaptic current driven by the NMDA receptor, an effect blocked by both a specific NMDA-site antagonist and a glycine-site antagonist. Even though glycine levels in the brain are high relative to the amount required to act as an NMDA receptor co-agonist, this work shows that GlyT1 removes glycine efficiently at the synapse, and that inhibition of GlyT1 can augment NMDA receptor function.

The present invention provides GlyT1 inhibitors as a treatment for disorders or conditions such as schizophrenia through its augmentation of glutamatergic neurotransmission.

SUMMARY OF THE INVENTION

The present invention relates to compounds of the Formula I,

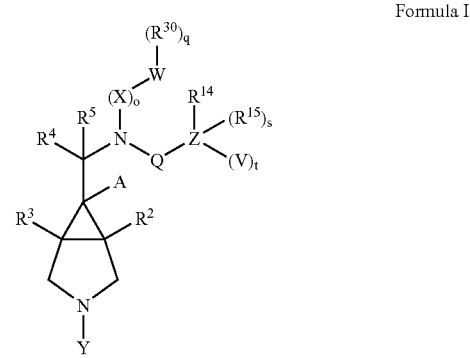

Formula I wherein:

Y is H or $(R^{100})_k$—$R^1$—$(R^6)_m$;

k is 0 or 1;

l=0, 1, 2 or 3;

m=1, 2 or 3;

n is 0, 1, 2, 3 or 4;

o is 0 or 1;

p is 0, 1, 2, or 3;

q is 0, 1, 2, 3 or 4;

r is 1 or 2;

s is 0, 1, 2, 3 or 4;

t is 0 or 1;

u is 1, 2, or 3;

v is 1, 2, or 3;

$R^{100}$ is —$CH_2$—, —$CH(C_1-C_3)$alkyl-, —C(=O)— or —$SO_2$—;

$R^1$ is —$(C_1-C_6)$alkyl, —$(C_3-C_8)$cycloalkyl, -(4 to 7 membered) heterocycloalkyl, —$(CH_2)_l$—$(C_6-C_{10}$ aryl) or -(5 to 10 membered) heteroaryl, or -(5 to 10 membered) tetrahydroheteroaryl;

each $R^6$ can be same or different and is independently selected from H, halo, —$(C_1-C_6)$alkyl-B, $(C_1-C_7)$ alkoxy-D, $(C_2-C_4)$alkenoxy, $(C_1-C_6)$alkyl-OH, —OH, CN, —$NO_2$, —$CR^7R^8R^9$, —$NR^{20}R^{21}$, —$NHCOalkyl(C_1-C_3)$, $NHSO_2alkyl(C_1-C_3)$, C(=O)$OR^{22}$, —$R^{23}$—C(=O)$OR^{22}$, —C(=O)$NH_2$, phenyl-E, phenoxy-F, morpholine, —$NR^{20}R^{21}$, aryl, heteroaryl, —S—$R^{24}$, and —$SO_2$—$R^{25}$;

B and D are each independently H, OH, phenyl, diphenyl or trifluro;

E and F are each independently H, alkyl, or halo;

$R^7$, $R^8$ and $R^9$ are each independently H, $(C_1-C_4)$alkyl, —OH, —O—$(C_1-C_4)$alkyl, —CN, —$NR^{26}R^{27}$ and —NHC (=O) $(C_1-C_3)$alkyl, wherein said alkyl groups are optionally substituted with OH, $OCH_3$, $NH_2$, NHC(=O)$(C_1-C_3)$alkyl, or $R^7$ and $R^8$ together with the carbon atom to which they are attached optionally form a $(C_3-C_7)$cycloalkyl ring, or a $(C_4-C_7)$heterocycloalkyl ring which contains 1-3 heteroatoms selected from N, O, S and optionally contains a C=O group;

$R^{20}$ and $R^{21}$ are each independently H or $(C_1-C_6)$ alkyl;

or $R^{20}$ and $R^{21}$ can be connected by 4 to 7 carbon atoms wherein from one to three of said carbon atoms can optionally be replaced with O, N or S, to form a heterocycloalkyl ring;

or $R^{20}$ and $R^{21}$ can be connected by 3 to 7 atoms selected from C, N, O or S to form a 5 to 10 membered heteroaryl ring;

$R^{22}$, $R^{23}$ and $R^{24}$ are each independently H, or $(C_1-C_5)$ alkyl;

$R^{25}$ is $(C_1-C_5)$alkyl;

$R^{26}$ and $R^{27}$ are each independently H or $(C_1-C_3)$alkyl;

or $R^{26}$ and $R^{27}$ can be connected by 4 to 7 carbon atoms to form a heterocycloalkyl ring;

$R^2$ and $R^3$ are each independently H or $(C_1-C_3)$alkyl;

$R^4$ and $R^5$ are each independently H or $(C_1-C_3)$ alkyl;

or $R^4$ and $R^5$ can be taken together form a double bond to an oxygen to form (C=O), or $R^4$ and $R^5$ are connected with 2 to 4 carbon atoms to form a 3-5 member carbocyclic ring;

A is H or $(C_1-C_3)$alkyl-$(R^{28})_n$;

$R^{28}$ is independently $(C_1-C_3)$alkoxy, —OH, —$NR^{12}R^{13}$ or —NHC(=O)$(C_1-C_4)$alkyl;

$R^{12}$ and $R^{13}$ are each independently H or —$(C_1-C_4)$alkyl; or $R^{12}$ and $R^{13}$ can be connected by 4 to 7 carbon atoms to form a heterocycloalkyl ring;

X is a bond, —$CH_2$—$(R^{29})_p$, —C(=O) or —$SO_2$;

$R^{29}$ is —$(C_1-C_3)$alkyl;

W is alkyl, —$(C_3-C_6)$cycloalkyl, -(3 to 7 membered) heterocycloalkyl, -(3 to 7 membered) heterocycloalkyl with 1 or 2 C=O groups, phenyl, or -(5 to 7 member) heteroaryl or heterocyclic;

$R^{30}$ is —$(C_1-C_4)$alkyl, —$(C_1-C_3)$alkoxy, CN, —F, —Cl, —Br, —I, —$NR^{18}R^{19}$, —NHC(=O)$R^{18}$, —$SCH_3$ or —C(=O)$CH_3$;

$R^{18}$ and $R^{19}$ are each independently H or —$(C_1-C_3)$alkyl;

Q is a bond, —CH—$(R^{31})_r$, —C(=O) or —$SO_2$;

$R^{31}$ is independently H or —$(C_1-C_3)$alkyl;

Z is —$(C_1-C_8)$alkyl, —$(C_3-C_8)$cycloalkyl, -(4 to 8 member) heterocycloalkyl, phenyl or -(5 to 7 membered) heteroaryl or heterocyclic;

$R^{14}$ is F, Cl, Br, I, V, H, —$NR^{16}R^{17}$, —$OR^{16}$, —C(=O)$NR^{16}R^{17}$, —$(SO_2)NR^{16}R^{17}$, or —$NR^{32}$—C=O—$R^{33}$, $R^{15}$ is —$(C_1-C_3)$alkyl, —$(C_1-C_3)$alkoxy, —F, —Br, —Cl, —I —OH or —CN;

V is —$(C_3-C_8)$cycloalkyl, —$(C_1-C_5)$alkyl, (5 to 7 membered) heterocycloalkyl, (5 to 7 membered)heterocycloalkyl substituted with 1 or 2 C=O groups or 1, 2, or 3 $(C_1-C_5)$alkyl groups;

$R^{16}$ and $R^{17}$ are each independently H, —$(C_1-C_6)$alkyl-$(R^{34})_u$, or $(C_3-C_8)$cycloalkyl-$(R^{35})_v$;

or $R^{16}$ and $R^{17}$ together with the nitrogen atom to which they are attached form a 4 to 7 membered heterocycloalkyl ring optionally containing from 1 to 3 additional heteroatoms independently selected from N, S and O, and contain C=O, wherein said heterocycloalkyl ring is optionally and independently substituted with 1 to 3 substituents independently selected from $(C_1-C_4)$ alkyl, OH, $(C_1-C_4)$alkoxy, $NH_2$, —NH(C=O)alkyl, —N$(C_1-C_3)$alkyl$)_2$, —C(=O)$CH_3$, $CONH_2$, $CO_2H$, $CH_2OH$, $CH_2Oalky(C_{2-4})$, and (5 to 7 membered) heterocycloalkyl;

$R^{32}$ and $R^{33}$ are each independently H or $(C_1-C_5)$alkyl;

or $R^{32}$ and $R^{33}$ can be taken together to form a 3-7 membered cycloalky ring, a 3-7 membered heterocycloalkyl ring with 1 to 3 heteroatoms, or a 5-7 membered heteroaryl ring with 1 to 3 heteroatoms;

$R^{34}$ and $R^{35}$ are each independently H, OH, $(C_1-C_5)$alkyl, $(C_2-C_4)$alkoxy, $NH_2$, NH(C=O)$(C_1-C_3)$alkyl, or a 5 to 7 membered heterocycloalkyl;

or $R^{34}$ and $R^{35}$ can be taken together to form a bridge containing 1-2 carbon atoms;

or pharmaceutically acceptable salts thereof.

This invention also relates to a method of treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia, and senile dementia of the Alzheimer's type) and memory disorders in a mammal, including a human, comprising administering to a mammal in need of such treatment an amount of a compound of the formula I a pharmaceutically acceptable salt thereof, that is effective in treating such condition or disorder.

This invention also relates to a pharmaceutical composition for treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia and senile dementia of the Alzheimer's type) and memory disorders in a mammal, including a human, comprising a compound of the formula I, or a pharmaceutically acceptable salt thereof, in an amount that is effective for treating such disorder or condition.

This invention also relates to a method of treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia and senile dementia of the Alzheimer's type) and memory disorders in a mammal, including a human, comprising administering to a mammal in need of such treatment a glycine transport-inhibiting amount of a compound of the formula I, or a pharmaceutically acceptable salt thereof.

This invention also relates to a pharmaceutical composition for treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia and senile dementia of the Alzheimer's type) and memory disorders in a mammal, including a human, comprising a compound of the formula I, or a pharmaceutically acceptable salt thereof, in a glycine transport-inhibiting amount.

The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^{3}H$ and $^{14}C$ are incorporated, are useful in drug and/or substrate tissue distribution assays. Tritium and $^{14}C$ isotopes are particularly preferred for their ease of preparation and detectability. Further, substitution with heavier isotopes such as deuterium can afford certain therapeutic advantages resulting from greater metabolic stability, for example increased in vivo half-life or reduced dosage requirements and, hence, can be preferred in some circumstances. Isotopically labelled compounds of formula I of this invention and prodrugs thereof can generally be prepared by carrying out the procedures disclosed in the Scheme and/or in the Examples and Preparations below, by substituting a readily available isotopically labelled reagent for a non-isotopically labelled reagent.

DETAILED DESCRIPTION OF THE INVENTION

The term "alkyl", as used herein, unless otherwise indicated, includes saturated monovalent hydrocarbon radicals having straight, branched or cyclic moieties or combinations thereof. Examples of "alkyl" groups include, but are not limited to, methyl, ethyl, propyl, isopropyl, butyl, iso-butyl, sec-butyl, tert-butyl, pentyl, hexyl, heptyl, 3-ethylbutyl, cyclopropyl, cyclobutyl, cyclopentyl, cyclohexyl, cycloheptyl, norbornyl, and the like.

The term "halo", as used herein, means chloro, fluoro, iodo or bromo.

The term "alkoxy", as used herein, means "alkyl-O—", wherein "alkyl" is defined as above.

The term "treating", as used herein, refers to reversing, alleviating, inhibiting the progress of, or preventing the disorder or condition to which such term applies, or one or more symptoms of such condition or disorder. The term "treatment", as used herein, refers to the act of "treating" is defined immediately above.

The term "bridge", as used herein, refers to a bridge, containing 1 or 2 carbons, linking two bridgeheads in a cyclic system to form a bicyclic compound.

As used herein, the expression "reaction inert solvent" refers to a solvent system in which the components do not interact with starting materials, reagents, or intermediates of products in a manner which adversely affects the yield of the desired product.

The compounds of formula I can have optical centers and therefore can occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or its intermediate.

Another embodiment of the invention relates to compounds of formula I, wherein the stereochemistry is defined as in formula II.

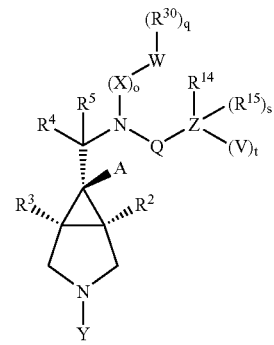

Formula II

Still another embodiment of the invention relates to compounds of formula I, wherein the stereochemistry is defined as in formula III:

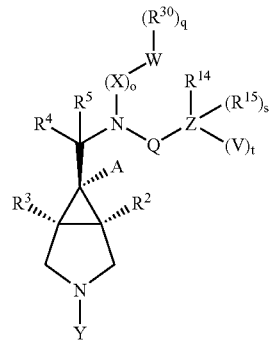

Formula III

Yet another embodiment of the invention relates to compounds of formula I, wherein examples of $C_6$-$C_{10}$ aryl include substituted and unsubstituted phenyl, indenyl, indanyl and naphthyl; examples of heterocycloalkyl include heterocyclic and the heterocyclic moiety of said heterocyclic-($C_1$-$C_8$) alkyl- are selected from saturated or unsaturated nonaromatic monocyclic or bicyclic ring systems, wherein said monocyclic ring systems contain from four to seven ring carbon atoms, from one to three of which can optionally be replaced with O, N, C=O or S; examples of heteroaryl include pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

In the definitions of hereinabove, Y can either be H or $(R^{100})_k$—$R^1$—$(R^6)_m$, wherein k is equal to 0 or 1. It is to be understood that when k is 0, $R^{100}$ is a bond so that $R^1$ is attached directly to the nitrogen atom of the bicyclic ring. As defined herein, $R^1$ is a bridging group connecting the N atom of the bicyclic ring with $R^6$. The portion of $R^1$ that is attached directly to $R^6$ can be mono, di-, or tri-substituted with $R^6$ depending upon whether m is one, two or three, respectively. For example, when m is equal to 2, Y is $(R^{100})_k$—$R^1$—$(R^6)_2$.

Compounds of formula I, above, and their pharmaceutically acceptable salts, can be prepared according to the following reaction Schemes I through VIII as discussed herein below. Unless otherwise indicated A, B, D, Q, V, W, X, Y, Z, $R^1$—$R^{35}$ and $R^{100}$ are defined as above. Isolation and purification of the products is accomplished by standard procedures, which are known to a chemist of ordinary skill.

The compounds of formula I, above, and the intermediates shown in the following reaction schemes can be isolated and purified by conventional procedures, such as recrystallization or chromatographic separation.

Insofar as the compounds of formula I of this invention can contain basic substituents, they are capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained.

The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, ptoluenesulfonate and pamoate (i.e., 1,1'-methylene-bis-(2-hydroxy-3-naphthoate))salts.

The compounds of the present invention exhibit significant glycine transport inhibiting activity and therefore are of value in the treatment of a wide variety of clinical conditions that are characterized by the deficit of glutamateric neurotransmission in mammalian subjects, especially humans. Such conditions include the positive and negative symptoms of schizophrenia and other psychoses, and cognitive deficits.

The compounds of this invention can be administered via either the oral, parenteral (such as subcutaneous, intraveneous, intramuscular, intrasternal and infusion techniques), rectal, intranasal or topical routes to mammals. In general, these compounds are most desirably administered to humans in doses ranging from about 1 mg to about 2000 mg per day, although variations will necessarily occur depending upon the weight and condition of the subject being treated and the particular route of administration chosen. However, a dosage level that is in the range of from about 0.1 mg to about 20 mg per kg of body weight per day is most desirably employed. Nevertheless, variations can still occur depending upon the species of animal being treated and its individual response to said medicament, as well as on the type of pharmaceutical formulation chosen and the time period and interval at which such administration is carried out. In some instances, dosage levels below the lower limit of the aforesaid range can be more than adequate, while in other cases still larger doses can be employed without causing any harmful side effects provided that such higher dose levels are first divided into several small doses for administration throughout the day.

In one embodiment, the compounds of this invention are administered as adjunctive therapy with known anti-psychotics such as Geodon.

The compounds of the present invention can be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they can be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine can be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type can also be employed as fillers in gelatine capsules; preferred materials in this connection also include lactose or milk sugar as well as high molecular weight polyethylene glycols. When aqueous suspensions and/or elixirs are desired for oral administration, the active ingredient can be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol can be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this can preferably be done by way of creams, jellies, gels, pastes, ointments and the like, in accordance with standard pharmaceutical practice.

The compounds of the present invention were assayed for their activity in inhibiting glycine reuptake in synaptosomes by first preparing synaptosomes and then measuring neurotransmitter reuptake activity as follows, the results of which are presented in Table 1 above: Male Sprague Dawley rats were decapitated and the brains removed. The whole brains were dissected out and placed in ice cold sucrose buffer; 1 gram in 20 mis (320 mM sucrose containing 1 mg/ml glucose, 0.1 mM EDTA and brought up to pH 7.4 with Tris base). The tissue was homogenized in a glass homogenizing tube with a teflon pestle at 350 RPMS using a Potters homogenizer. The homogenate was centrifuged at 1000×g for 10 min at 4° C. The resulting supernatant was recentrifuged at 17,000×g for 20 min at 4° C. The final pellet was resuspended in an appropriate volume of sucrose buffer containing 5 mM alanine, to yield less than 10% uptake.

The uptake assays were conducted in 96 well matrix plates. Each well contained 25 μL of solvent, inhibitor or 10 mM glycine for nonspecific uptake, 200 μL of [$^3$H]-glycine (40 nM final), made up in modified Krebs containing 5 mM alanine and glucose (1 mg/ml) and 25 μL of synaptosomes. The plates were then incubated at room temperature for the 15 min. The incubation was terminated by filtration through GF/B filters, using a 96 well Brandel Cell Harvester. The filters were washed with modified Krebs buffer and either counted in a liquid scintillation counter or in a LKB Beta Plate counter. Compounds of the invention analyzed by this assay have been found to have significant activity in inhibiting glycine reuptake in synaptosomes, having $IC_{50}$ values more potent than 10 μM.

The present invention is illustrated by the examples shown in tables 1 & 2 and preparations below. However, it should be understood that the invention is not limited to the specific details of these examples. Melting points were taken with a Buchi micro melting point apparatus and uncorrected. Infrared Ray absorption spectra (IR) were measured by a Shimazu infrared spectrometer (IR-470). $^1$H and $^{13}$C nuclear magnetic resonance spectra (NMR) were measured in $CDCl_3$ by a Varian NMR spectrometer (Unity, 400 MHz for $^1$H, 100 MHz for $^{13}$C) unless otherwise indicated and peak positions are expressed in parts per million (ppm) downfield from tetramethylsilane (δ). The peak shapes are denoted as follows: s, singlet; d, doublet; t, triplet; m, multiplet; br, broad.

A pharmaceutical composition for treating a disorder or condition selected from psychosis, schizophrenia, conduct disorder, disruptive behavior disorder, bipolar disorder, psychotic episodes of anxiety, anxiety associated with psychosis, psychotic mood disorders selected from severe major depressive disorder; mood disorders associated with psychotic disorders selected from acute mania and depression associated with bipolar disorder, and mood disorders associated with schizophrenia; behavioral manifestations of mental retardation, conduct disorder and autistic disorder; movement disorders selected from Tourette's syndrome, akinetic-rigid syndrome, movement disorders associated with Parkinson's disease, tardive dyskinesia and other drug-induced and neurodegeneration-based dyskinesias; attention deficit hyperactivity disorder; cognitive disorders selected from dementias, age-related dementia and senile dementia of the Alzheimer's type; and memory disorders in a mammal, comprising an amount of a compound according to claim 1 that is effective in treating such disorder or condition.

During any of the following synthetic sequences it can be necessary and/or desirable to protect sensitive or reactive groups on any of the molecules concerned. This can be achieved by means of conventional protecting groups, such as those described in T. W. Greene, *Protective Groups in Organic Chemistry*, John Wiley & Sons, 1981; and T. W. Greene and P. G. M. Wuts, *Protective Groups in Organic Chemistry*, John Wiley & Sons, 1991, which are hereby incorporated by reference.

Compounds of formula I, above, and their pharmaceutically acceptable salts, can be prepared according to the following reaction Schemes I through VII as discussed herein below. Unless otherwise indicated A, B, D, Q, V, W, X, Y, Z, $R^1$—$R^{35}$ and $R^{100}$ are defined as above. Isolation and purification of the products is accomplished by standard procedures, which are known to a chemist of ordinary skill.

The following schemes are exemplary of the processes for making compounds of formula I.

Scheme I illustrates a method for the preparation of compounds having the basic structure of formula I, where A is hydrogen, X is C=O or $SO_2$, W is 2-thiophene, Q is a single bond or a methylene group, Y is H, $R^2$ and $R^3$ are H, and Z, $R^{14}$, $R^{15}$, and V are described as above.

Referring to Scheme I, a compound of formula (I) [*SynLeft*, 1996, 1097] can be treated with $(BOC)_2O$ in the presence of a suitable base such as triethylamine, in solvents such as $CH_2Cl_2$, to produce the desired carbamate of formula (II). Oxidation of the primary alcohol under Swern conditions with DMSO and oxayl chloride, in the presence of a suitable base such as triethyl amine (TEA) or diisopropylethylamine (DIEA), in solvents such as $CH_2Cl_2$ or 1,2-dichloroethane (DCE), at temperatures ranging from −78° C. to room temperature, preferably at about room temperature, to produce the corresponding aldehyde (not depicted). Other suitable oxidation reagents for this transformation include TPAP/NMO or PCC.

Treatment of the aldehyde with an appropriately substituted amine or aniline reagent of forumula (III) and a suitable reducing agent such as $NaCNBH_3$, in a solvent such as MeOH, at temperatures ranging from −5° C. to room temperature, preferably at about room temperature, produced the desired amine of formula (IV). Other suitable reducing agents for this reaction include $NaBH_4$ or $NaHB(OAc)_3$, in solvents such as MeOH, $CH_2Cl_2$ or DCE. Other suitable conditions for this transformation include treatment of the corresponding aldehyde with the amine reagent (III) in $CH_2Cl_2$ or DCE in the presence of 4 A molecular sieves and a base such as TEA at room temperature, followed by treatment with $NaHB(OAc)_3$.

Scheme I

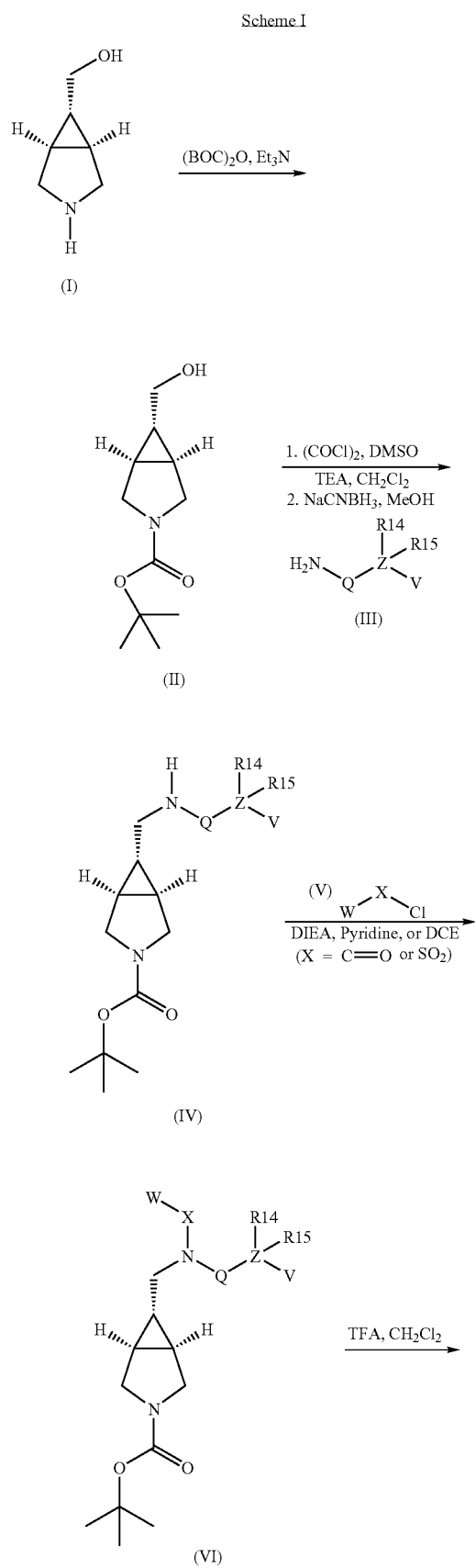

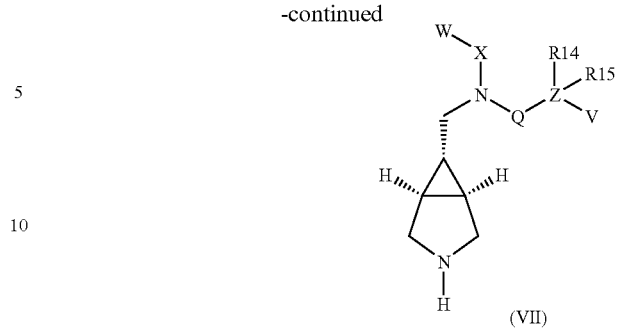

Compounds of formula (VI) can be prepared by treatment of an amine of formula (IV) with an appropriately substituted acid chloride or sulfonyl chloride reagent of formula (V) in the presence of a suitable base such as DIEA, pyridine or TEA, in solvents such as DCE or $CH_2Cl_2$, at temperatures ranging from room temperature to about the reflux temperature, preferably at about room temperature, to produce the corresponding compound of formula (VI). Finally, compounds of formula (VII) can be prepared by treatment of a carbamate of formula (VI) with TFA, in solvents such as $CH_2Cl_2$ or DCE, at temperatures ranging from 0° C. to about room temperature, preferably at about room temperature, to produce the corresponding amine of formula (VII).

Scheme II illustrates a method for the preparation of compounds having the basic structure of formula I where A is hydrogen, X is C=O or $SO_2$, W is 2-thiophene, Q is a single bond or a methylene group, $R^{100}$ is a methylene ($CH_2$) or substituted methylene, $R^2$ and $R^3$ are H, and Z, $R^{14}$, $R^{15}$, $R^1$, $R^6$, m, V and Y are described as above.

Referring to scheme II below, compounds of formula (VIII) can be prepared by treatment of an amine of formula (VII) with an appropriately substituted aldehyde or ketone and a reducing agent such as $NaHB(OAc)_3$, in solvents such as $CH_2Cl_2$ or DCE, at temperatures ranging from 0° C. to about room temperature, preferably at about room temperature, to produce the corresponding amine of formula (VII). Other suitable conditions for this process include treatment of the amine of formula (VII) with an aldehyde in toluene, at about the reflux temperature; followed by treatment with $NaBH_4$, in solvents such as MeOH, produce the corresponding amine of formula (VIII). Also, treatment of an amine of formula (VII) with an aldehyde and $NaCNBH_3$ in a solvent such as MeOH, produce the corresponding amine of formula (VIII).

Scheme II

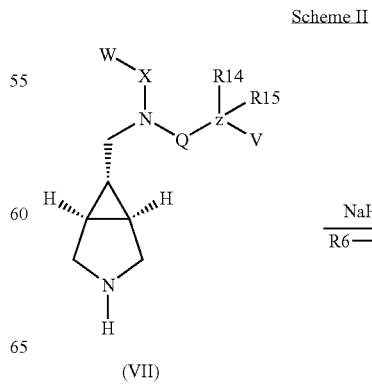

-continued

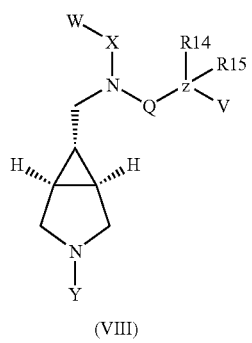

(VIII)

Scheme III illustrates a method for the preparation of compounds having the basic structure of formula I, where A is hydrogen, X is C=O or $SO_2$, W is 2-thiophene, Q is a single bond or a methylene group, $R^{100}$ is C=O or $SO_2$, $R^2$ and $R^3$ are H, and Z, $R^{14}$, $R^{15}$, $R^1$, $R^6$, V and Y are described as above.

Referring to scheme III below, compounds of formula (VIII), where $R^{100}$=C=O, can be prepared by treatment of compounds of formula (VII) with an appropriately substituted acid chloride ($R^{100}$=C=O) reagent of formula (IX) in the presence of a suitable base such as DIEA, in solvents such as $CH_2Cl_2$ or DCE, at temperature ranging from 0° C. to about room temperature, preferably at about room temperature, to produce the corresponding compounds of formula (VIII). Furthermore, compounds of formula (VIII), where $R^{100}$=$SO_2$, can be prepared by treatment of compounds of formula (VII) with an appropriately substituted sulfonyl chloride ($R^{100}$=$SO_2$) reagent of formula (IX), in the presence of a suitable base such as DIEA or TEA, in solvents such as $CH_2Cl_2$ or DCE, at temperatures ranging from room temperature to about the reflux temperature, preferably at about the reflux temperature, to produce compounds of formula (VIII).

Scheme III

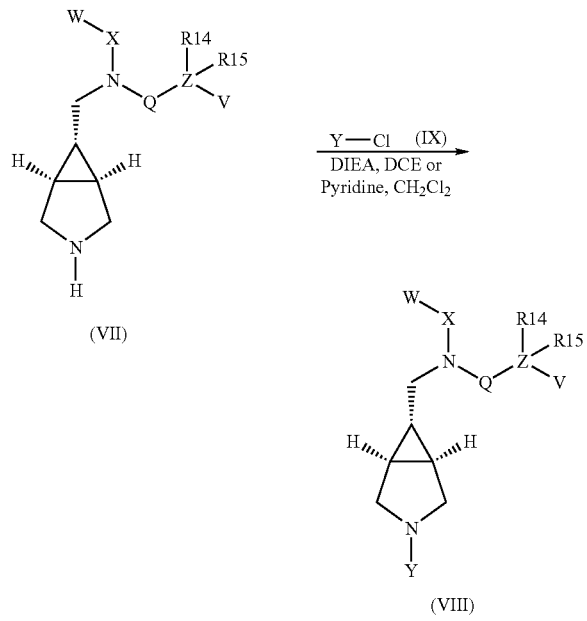

Scheme IV illustrates a method for the preparation of compounds having the basic structure of formula I, where A is hydrogen, X is C=O, Q is a single bond or a methylene group, $R^{100}$ is C=O or $SO_2$, $R^2$ and $R^3$ are H, and W, q, $R^{30}$, Z, $R^{14}$, $R^{15}$, $R^1$, $R^6$, V and Y are described as above.

Referring to scheme IV below, compounds of formula (XII) can be prepared by treatment of compounds of formula (X) with an appropriately substituted acid chloride reagent of formula (XI) in the presence of a suitable base such as pyridine, DIEA or TEA, in solvents such as $CH_2Cl_2$ or DCE, at temperature ranging from 0° C. to about room temperature, preferably at about room temperature, to produce the corresponding compounds of formula (XII).

Scheme IV

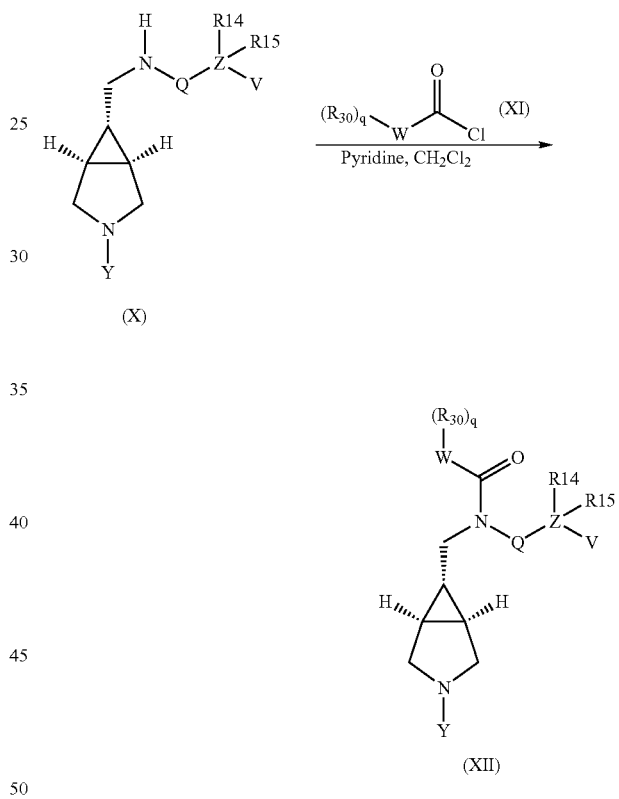

(XII)

Scheme V illustrates a method for the preparation of compounds having the basic structure of formula I, where A is hydrogen, X is a methylene ($CH_2$), Q is a single bond or a methylene group, $R^{100}$ is C=O or $SO_2$, $R^2$ and $R^3$ are H, and W, o, q, $R^{30}$, Z, $R^{14}$, $R^{15}$, $R^1$, $R^6$, V and Y are described as above.

Referring to scheme V below, compounds of formula (X) can be treated with a suitable base such as NaH or KH, and an appropriately substituted alkylating agent of formula (XIII), where L is a suitable leaving group such as Cl, Br, I, OMs, OTs, in solvents such as THF or ether, at temperatures ranging from 0° C. to about room temperature, preferably at about room temperature, to produce the compounds of formula (XIV).

Scheme V

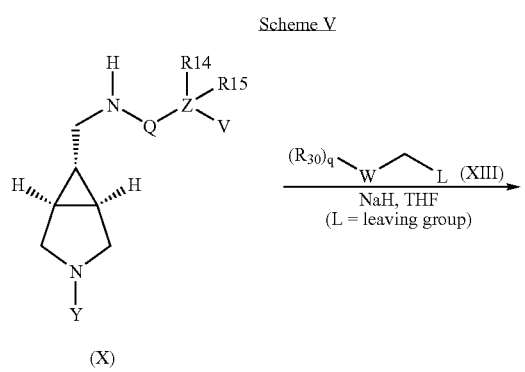

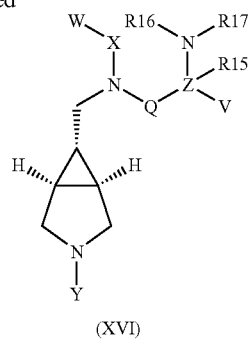

(XVI)

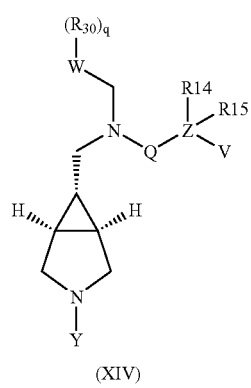

(XIV)

Scheme VI illustrates a method for the preparation of compounds having the basic structure of formula I, where A is hydrogen, Q is a single bond or a methylene group, $R^{100}$ is C=O, $CH_2$ or $SO_2$, $R^2$ and $R^3$ are H, and X, W, q, $R^{30}$, Z, $R^{14}$, $R^{15}$, $R^1$, $R^6$, V and Y are described as above.

Referring to scheme VI below, treatment of a compound of formula (XV) with an appropriately substituted primary or secondary amine ($HNR^{16}R^{17}$), a suitable catalyst such as palladium (II) acetate and BINAP, and a base, such as sodium tert-butoxide, in solvents such as toluene, at temperatures ranging from room temperature to about the reflux temperature, preferably, at about the reflux temperature, produces the desired compound of formula (XVI).

Scheme VI

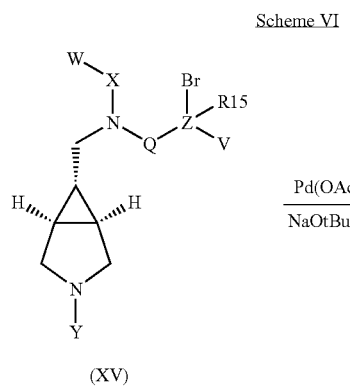

Alternatively, compounds of formula (XVI), wherein the Z group is a heteroaryl moiety, such as pyridine group, can be prepared by the alternative method described below. Referring to scheme VII below, treatment of a compound of formula (XVII), wherein halogen is bromo or chloro, neat in an appropriately substituted primary or secondary amine reagent ($HNR^{16}R^{17}$), at temperatures ranging from 50° C. to about 180° C., preferably, at about 150° C. produces the desired compound of formula (XVI). Alternative conditions for this reaction can include treatment of compounds of formula (XVII) with an amine reagent ($HNR^{16}R^{17}$) in solvents such as DMF or DMP, at temperatures ranging from room temperature to about the reflux temperature to produce the corresponding compounds of formula (XVI).

Scheme VII

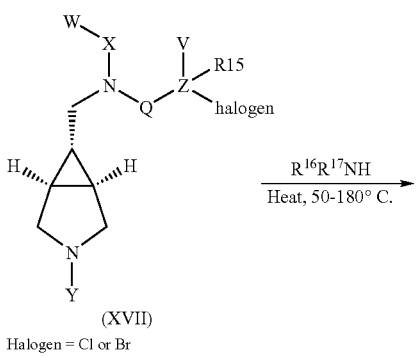

Halogen = Cl or Br

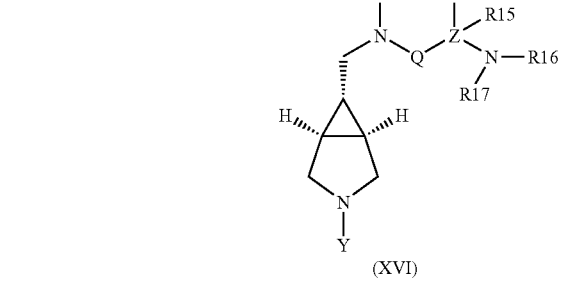

In the above schemes it is noted that $R^6$ is H. However, the present invention contemplates schemes when $R^6$ is other than H, as defined herein. The chemistry shown in the above schemes is applicable in those cases where $R^6$ is other than hydrogen. However, if any of the substituents in $R^6$ are reactive with the reactants or intermediates, then $R^6$ can be protected with a protecting group using techniques known to skilled in the art such as those described above.

The following Examples illustrate the present invention. It is to be understood, however, that the invention, as fully described herein and as recited in the claims, is not intended to be limited by the details of the following examples.

EXAMPLES

Preparation 1

6Hydroxymethyl-3-aza-bicyclo[3.1.0]hexane-3-carboxylic acid tert-butyl ester

To a solution of (3-Aza-bicyclo[3.1.0]hex-6-yl)-methanol-HCl (11.8 gm, 78.7 mmol) in 350 mL of anhydrous CH$_2$Cl$_2$ at room temperature was added Et$_3$N (32.9 mL, 236 mmol), followed by (BOC)$_2$O (18.9 gm, 86.6 mmol) in portions. The reaction was stirred at room temperature for 18 hours. The mixture was washed with saturated NaHCO$_3$, water, brine and dried over anhydrous MgSO$_4$. The mixture was filtered and concentrated under reduced pressure to yield the crude material, which was purified via flash chromatography with 10% MeOH/EtOAc. The product containing fractions were collected and concentrated to yield the desired product (15.6 gm). 400 MHz $^1$H NMR (CDCl$_3$) δ 3.42-3.56 (m, 4H), 3.24-3.37 (m, 2H), 1.72 (brs, 1H), 1.37-1.41 (m, 10H), 0.87-0.93 (m, 1H); MS (M+1) 213.2.

Preparation 2

6-[(3-Fluoro-4-morpholin-4-yl-phenylamino)-methyl]-3-aza-bicyclo[3.1.0]hexane-3-carboxylic acid tert-butyl ester To a stirring solution of oxalyl chloride (0.49 mL, 5.63 mmol) in 30 mL of anhydrous CH$_2$Cl$_2$ at −78° C. was added DMSO (0.87 mL, 12.2 mmol) dropwise. After 10 minutes, 6-Hydroxymethyl-3-aza-bicyclo[3.1.0]hexane-3-carboxylic acid tert-butyl ester (1.0 gm, 4.69 mmol) in 10 mL anhydrous CH$_2$Cl$_2$ was added. After the mixture stirred 30 minutes, triethylamine (3.24 mL, 23.4 mmol) was added and the mixture was allowed to slowly warm to 0° C. over 1 hour. The mixture was concentrated, the resulting solid was taken up in saturated NaHCO$_3$ and EtOAc, the layers were separated and the aqueous layer was extracted with EtOAc. The combined organic layers were dried, filtered and concentrated to yield the crude aldehyde, which was used in the next step without purification.

To a stirring solution of the aldehyde prepared above (991 mg, 4.69 mmol) in 30 mL of MeOH was added 3-fluoro-4-morpholinoaniline (920 mg, 4.69 mmol), AcOH (0.38 mL, 6.56 mmol) and NaCNBH$_3$ (295 mg, 4.69 mmol). The reaction mixture was stirred at room temperature for 90 minutes. The mixture was concentrated under reduced pressure and the resulting material was taken up in saturated NaHCO$_3$ and extracted with CH$_2$Cl$_2$. The combined organic layers were dried over anhydrous MgSO$_4$, filtered and concentrated under reduced pressure. The resulting crude material was purified by flash chromatography with 50 % EtOAc/hexanes. The product containing fractions were collected and concentrated to yield 1.3 gm of the desired amine. 400 MHz $^1$H NMR (CDCl$_3$) δ 6.74-6.81 (m, 1H), 6.30-6.42 (m, 2H), 3.81-3.83 (m, 4H), 3.61 (brs, 1H), 3.59 (d, J=10.8 Hz, 1H), 3.51 (d, J=10.8 Hz, 1H), 3.32 (t, J=9.5 Hz, 2H), 2.93 (brs, 6H), 1.40 (s, 11H), 0.87-0.92 (m, 1H); MS (M+1) 392.2.

Preparation 3

6-{[(3-Fluoro-4-morpholin-4-yl-phenyl)-(thiophene-2-carbonyl)-amino]-methyl}-3-aza-bicyclo[3.1.0]hexane-3-carboxylic acid tert-butyl ester To a stirring solution of 6-[(3-Fluoro-4-morpholin-4-yl-phenylamino)-methyl]-3-aza-bicyclo[3.1.0]hexane-3-carboxylic acid tert-butyl ester prepared above (500 mg, 1.28 mmol) in 10 mL of DCE at room temperature was added DIEA (0.33 mL, 1.92 mmol) and 2-thiophenecarbonylchloride (0.21 mL, 1.92 mmol). After 2 hours, saturated NaHCO$_3$ was added, and the mixture was extracted with CH$_2$Cl$_2$. The combined extracts were dried over anhydrous MgSO$_4$, filtered and concentrated under reduced pressure. The resulting crude material was taken up in 50% EtOAc/hexanes and the white solids were filtered off. The remaining filtrate was concentrated under reduce pressure to yield 640 mg of the desired product. 400 MHz $^1$H NMR (CDCl$_3$) δ 7.26-7.28 (m, 1H), 6.83-7.15 (m, 4H), 6.76-6.78 (m, 1H), 3.79-3.85 (m, 5H), 3.54-3.59 (m, 1H), 3.44 (d, J=11.0 Hz, 1H), 3.39 (d, J=11.0 Hz, 1H), 3.21-3.26 (m, 2H), 3.08-3.10 (m, 4H), 1.36-1.38 (m, 11H), 0.81-0.86 (m, 1H); MS M+1)

Preparation 4

Thiophene-2-carboxylic acid (3-aza-bicyclo[3.1.0]hex-6-ylmethyl)-(3-fluoro-4-morpholin-4-yl-phenyl)-amide trifluoroacetic acid salt To a stirring solution of 6-{[(3-Fluoro-4-morpholin-4-yl-phenyl)-(thiophene-2-carbonyl)-amino]methyl}-3-aza-bicyclo[3.1.0]hexane-3-carboxylic acid tert-butyl ester prepared above (640 mg, 1.28 mmol) in 6 mL of CH$_2$Cl$_2$ at room temperature was added 6 mL of TFA. The reaction stirred at room temperature for 1 hour. The mixture was concentrated under reduced pressure, taken up in toluene and concentrated again to yield 854 mg of the desired product. 400 MHz $^1$H NMR (CDCl$_3$) δ 9.06 (brs, 1H), 8.62 (brs, 1H), 7.33-7.35 (m, 1H), 7.21-7.25 (m, 1H), 6.94-7.11 (m, 2H), 6.88-6.92 (m, 1H), 6.81-6.84 (m, 1H), 3.89-3.91 (m, 4H), 3.72 (d, J=7.05 Hz, 2H), 3.39-3.46 (m, 4H), 3.16-3.18 (m, 4H), 1.77 (brs, 2H), 1.35-1.37 (m, 1H); MS (M+1) 402.1

Example 1

Thiophene-2-carboxylic acid (3-benzyl-3-aza-bicyclo[3.1.0]hex-6-ylmethyl)-(3-fluoro-4-morpholin-4-yl-phenyl)-amide To a stirring solution of the Thiophene-2-carboxylic acid (3-aza-bicyclo[3.1.0]hex-6-ylmethyl)-(3-fluoro-4-morpholin-4-yl-phenyl)-amide trifluoroacetic acid salt prepared above (100 mg, 0.16 mmol) in 4 mL of CH$_2$Cl$_2$ at room temperature was added benzaldehyde (0.02 mL, 0.24 mmol) and NaHB(OAc)$_3$ (50 mg, 0.24 mmol). The reaction stirred at room temperature for 2 hours. The reaction was quenched by the addition of saturated NaHCO$_3$, the layers were separated, and the aqueous layer was extracted with CH$_2$Cl$_2$. The combined organic layers were dried over anhydrous MgSO$_4$, filtered and concentrated under reduced pressure. The resulting crude material was purified via flash chromatography with 75% EtOAc/hexanes. The product containing fractions were collected and concentrated to yield 32 mg of the desired product. 400 MHz $^1$H NMR (CDCl$_3$) δ 7.17-7.29 (m, 6H), 6.94-6.98 (m, 4H), 6.78-6.80 (m, 1H), 3.86-3.88 (m, 4H), 3.65 (d, J=7.47 Hz, 2H), 3.52 (brs, 2H), 3.09-3.12 (m, 4H), 2.86-2.88 (m, 2H), 2.26-2.28 (m, 2H), 1.63 (brs, 1H), 1.47 (brs, 1H), 1.21-1.25 (m, 1H); MS (M+1) 492.2.

General Procedure for the Reductive Alkylation Preparation of Compounds of Formula VIII To a stirring solution of 1.0 equiv. of a compound of formula (VII) in methylene chloride (0.2 M) at room temperature was added the appropriately substituted aldehyde reagent (2.0 equiv.), acetic acid (2.0 equiv.) and sodium triacetoxyborohydride (2.0 equiv.). The reaction mixtures were stirred at room temperature for up to 24 hours. The mixtures were then quenched by the addition of saturated sodium bicarbonate solution and extracted with methylene chloride. The combined organic layers were dried over anhydrous $MgSO_4$ and concentrated under reduced pressure. The resulting crude material was purified by flash chromatography to yield the desired tertiary amines in 40-95% yield.

The following compounds were made using the above procedure of Example 1, starting with the appropriate starting amine of formula (VII) and the appropriate aldehyde reagent. Furthermore, pharmaceutically acetable salts of the compounds listed below can be prepared as follows. To a stirring solution of compounds of the general formula (VIII) (prepared as described above in Example 1, 1.0 equiv.) in a suitable solvent such as methyl ethyl ketone, methylene chloride/methanol (1:1) or methanol (0.1 M) at room temperature was added the appropriate acid, such as hydrochloric acid, citric acid, p-toluenesulfonic acid, methansulfonic acid or benzene sulfonic acid (2-3 equiv) in one portion. The resulting mixture was stirred at room temperature for up to 18 hours, during which time a precipitate formed. Filtration of the solid and drying under reduced pressure afforded the desired salts.

Thiophene-2-carboxylic acid [3-(4-ethyl-benzyl)-3-aza-bicyclo[3.1.0]hex-6-ylmethyl]-(3-fluoro-4-morpholin-4-yl-phenyl)-amide 400 MHz $^1$H NMR (CDCl$_3$) δ 7.27-7.29 (m, 1H), 7.07-7.13 (m, 4H), 6.90-6.98 (m, 2H), 6.84-6.89 (m, 2H), 6.78-6.80 (m, 1H), 3.86-3.88 (m, 4H), 3.65 (d, J=7.47 Hz, 2H), 3.50 (brs, 2H), 3.09-3.11 (m, 4H), 2.86-2.89 (m, 2H), 2.59 (q, 2H), 2.28-2.29 (m,2H), 1.47 (brs, 1H), 1.17-1.27 (m, 5H); MS (M+1) 520.2.

| Compound ID | IUPAC NAME |
|---|---|
| 1 | Thiophene-2-carboxylic acid (3-cyclohexylmethyl-3-aza-bicyclo[3.1.0]hex-6-ylmethyl)-(3-fluoro-4-morpholin-4-yl-phenyl)-amide |
| 2 | Thiophene-2-carboxylic acid (3-fluoro-4-morpholin-4-yl-phenyl)-[3-(4-methyl-benzyl)-3-aza-bicyclo[3.1.0]hex-6-ylmethyl]-amide |
| 3 | Thiophene-2-carboxylic acid (3-fluoro-4-morpholin-4-yl-phenyl)-[3-(4-methoxy-benzyl)-3-aza-bicyclo[3.1.0]hex-6-ylmethyl]-amide |
| 4 | Thiophene-2-carboxylic acid (3-fluoro-4-morpholin-4-yl-phenyl)-[3-(2-hydroxy-indan-2-ylmethyl)-3-aza-bicyclo[3.1.0]hex-6-ylmethyl]-amide |
| 5 | Thiophene-2-carboxylic acid (3-fluoro-4-morpholin-4-yl-phenyl)-[3-(1-hydroxy-cyclohexylmethyl)-3-aza-bicyclo[3.1.0]hex-6-ylmethyl]-amide |
| 6 | Thiophene-2-carboxylic acid [3-(4-butyl-benzyl)-3-aza-bicyclo[3.1.0]hex-6-ylmethyl]-(3-fluoro-4-morpholin-4-yl-phenyl)-amide |
| 7 | Thiophene-2-carboxylic acid (3-fluoro-4-morpholin-4-yl-phenyl)-(3-pyridin-3-ylmethyl-3-aza-bicyclo[3.1.0]hex-6-ylmethyl)-amide |
| 8 | Thiophene-2-carboxylic acid [3-(4-chloro-benzyl)-3-aza-bicyclo[3.1.0]hex-6-ylmethyl]-(3-fluoro-4-morpholin-4-yl-phenyl)-amide |
| 9 | Thiophene-2-carboxylic acid [3-(4-fluoro-benzyl)-3-aza-bicyclo[3.1.0]hex-6-ylmethyl]-(3-fluoro-4-morpholin-4-yl-phenyl)-amide |
| 10 | Thiophene-2-carboxylic acid [3-(2-ethyl-5-methyl-3H-imidazol-4-ylmethyl)-3-aza-bicyclo[3.1.0]hex-6-ylmethyl]-(3-fluoro-4-morpholin-4-yl-phenyl)-amide |
| 11 | Thiophene-2-carboxylic acid (3-fluoro-4-morpholin-4-yl-phenyl)-[3-(2-p-tolyl-ethyl)-3-aza-bicyclo[3.1.0]hex-6-ylmethyl]-amide |
| 12 | Thiophene-2-carboxylic acid (3-fluoro-4-morpholin-4-yl-phenyl)-(3-thiophen-2-ylmethyl-3-aza-bicyclo[3.1.0]hex-6-ylmethyl)-amide |
| 13 | Thiophene-2-carboxylic acid (3-fluoro-4-morpholin-4-yl-phenyl)-(3-quinolin-2-ylmethyl-3-aza-bicyclo[3.1.0]hex-6-ylmethyl)-amide |
| 14 | Thiophene-2-carboxylic acid (3-fluoro-4-morpholin-4-yl-phenyl)-[3-(4-nitro-benzyl)-3-aza-bicyclo[3.1.0]hex-6-ylmethyl]-amide |
| 15 | Thiophene-2-carboxylic acid (3-fluoro-4-morpholin-4-yl-phenyl)-[3-(3-methyl-benzyl)-3-aza-bicyclo[3.1.0]hex-6-ylmethyl]-amide |
| 16 | Thiophene-2-carboxylic acid (3-fluoro-4-morpholin-4-yl-phenyl)-[3-(3,4,5-trimethoxy-benzyl)-3-aza-bicyclo[3.1.0]hex-6-ylmethyl]-amide |
| 17 | Thiophene-2-carboxylic acid (3-fluoro-4-morpholin-4-yl-phenyl)-(3-pyridin-2-ylmethyl-3-aza-bicyclo[3.1.0]hex-6-ylmethyl)-amide |
| 18 | Thiophene-2-carboxylic acid [3-(3,4-dichloro-benzyl)-3-aza-bicyclo[3.1.0]hex-6-ylmethyl]-(3-fluoro-4-morpholin-4-yl-phenyl)-amide |
| 19 | Thiophene-2-carboxylic acid (3-fluoro-4-morpholin-4-yl-phenyl)-[3-(3-methoxy-benzyl)-3-aza-bicyclo[3.1.0]hex-6-ylmethyl]-amide |
| 20 | Thiophene-2-carboxylic acid (3-fluoro-4-morpholin-4-yl-phenyl)-[3-(5-hydroxymethyl-furan-2-ylmethyl)-3-aza-bicyclo[3.1.0]hex-6-ylmethyl]-amide |
| 21 | Thiophene-2-carboxylic acid (3-fluoro-4-morpholin-4-yl-phenyl)-[3-(1H-indol-3-ylmethyl)-3-aza-bicyclo[3.1.0]hex-6-ylmethyl]-amide |
| 22 | Thiophene-2-carboxylic acid (3-fluoro-4-morpholin-4-yl-phenyl)-(3-pyridin-4-ylmethyl-3-aza-bicyclo[3.1.0]hex-6-ylmethyl)-amide |
| 23 | Thiophene-2-carboxylic acid (3-fluoro-4-morpholin-4-yl-phenyl)-[3-(2-methyl-benzyl)-3-aza-bicyclo[3.1.0]hex-6-ylmethyl]-amide |

-continued

| Compound ID | IUPAC NAME |
|---|---|
| 24 | Thiophene-2-carboxylic acid (3-fluoro-4-morpholin-4-yl-phenyl)-[3-(3-phenoxy-benzyl)-3-aza-bicyclo[3.1.0]hex-6-ylmethyl]-amide |
| 25 | Thiophene-2-carboxylic acid (3-fluoro-4-morpholin-4-yl-phenyl)-(3-naphthalen-1-ylmethyl-3-aza-bicyclo[3.1.0]hex-6-ylmethyl)-amide |
| 26 | Thiophene-2-carboxylic acid (3-fluoro-4-morpholin-4-yl-phenyl)-(3-phenethyl-3-aza-bicyclo[3.1.0]hex-6-ylmethyl)-amide |
| 27 | Thiophene-2-carboxylic acid (3-benzo[1,3]dioxol-5-ylmethyl-3-aza-bicyclo[3.1.0]hex-6-ylmethyl)-(3-fluoro-4-morpholin-4-yl-phenyl)-amide |
| 28 | Thiophene-2-carboxylic acid (3-fluoro-4-morpholin-4-yl-phenyl)-(3-naphthalen-2-ylmethyl-3-aza-bicyclo[3.1.0]hex-6-ylmethyl)-amide |
| 29 | Thiophene-2-carboxylic acid [3-(2,2-diphenyl-ethyl)-3-aza-bicyclo[3.1.0]hex-6-ylmethyl]-(3-fluoro-4-morpholin-4-yl-phenyl)-amide |
| 30 | Thiophene-2-carboxylic acid (3-fluoro-4-morpholin-4-yl-phenyl)-(3-quinolin-4-ylmethyl-3-aza-bicyclo[3.1.0]hex-6-ylmethyl)-amide |
| 31 | Thiophene-2-carboxylic acid (3-fluoro-4-morpholin-4-yl-phenyl)-(3-quinolin-3-ylmethyl-3-aza-bicyclo[3.1.0]hex-6-ylmethyl)-amide |
| 32 | Thiophene-2-carboxylic acid (3-fluoro-4-morpholin-4-yl-phenyl)-[3-(3-trifluoromethoxy-benzyl)-3-aza-bicyclo[3.1.0]hex-6-ylmethyl]-amide |
| 33 | Thiophene-2-carboxylic acid (3-fluoro-4-morpholin-4-yl-phenyl)-[3-(3-methyl-benzo[b]thiophen-2-ylmethyl)-3-aza-bicyclo[3.1.0]hex-6-ylmethyl]-amide |
| 34 | Thiophene-2-carboxylic acid (3-benzofuran-2-ylmethyl-3-aza-bicyclo[3.1.0]hex-6-ylmethyl)-(3-fluoro-4-morpholin-4-yl-phenyl)-amide |
| 35 | Thiophene-2-carboxylic acid (3-fluoro-4-morpholin-4-yl-phenyl)-(3-quinoxalin-6-ylmethyl-3-aza-bicyclo[3.1.0]hex-6-ylmethyl)-amide |
| 36 | Thiophene-2-carboxylic acid (3-fluoro-4-morpholin-4-yl-phenyl)-[3-(2-fluoro-5-trifluoromethyl-benzyl)-3-aza-bicyclo[3.1.0]hex-6-ylmethyl]-amide |
| 37 | Thiophene-2-carboxylic acid (3-fluoro-4-morpholin-4-yl-phenyl)-{3-[4-(2-hydroxy-ethoxy)-benzyl]-3-aza-bicyclo[3.1.0]hex-6-ylmethyl}-amide |
| 38 | Thiophene-2-carboxylic acid (3-fluoro-4-morpholin-4-yl-phenyl)-[3-(4-methanesulfonyl-benzyl)-3-aza-bicyclo[3.1.0]hex-6-ylmethyl]-amide |
| 39 | Thiophene-2-carboxylic acid (3-fluoro-4-morpholin-4-yl-phenyl)-[3-(1-methyl-1H-pyrrol-2-ylmethyl)-3-aza-bicyclo[3.1.0]hex-6-ylmethyl]-amide |
| 40 | Thiophene-2-carboxylic acid (3-fluoro-4-morpholin-4-yl-phenyl)-(3-furan-3-ylmethyl-3-aza-bicyclo[3.1.0]hex-6-ylmethyl)-amide |
| 41 | Thiophene-2-carboxylic acid (3-fluoro-4-morpholin-4-yl-phenyl)-(3-thiophen-3-ylmethyl-3-aza-bicyclo[3.1.0]hex-6-ylmethyl)-amide |
| 42 | Thiophene-2-carboxylic acid (3-fluoro-4-morpholin-4-yl-phenyl)-[3-(4-trifluoromethoxy-benzyl)-3-aza-bicyclo[3.1.0]hex-6-ylmethyl]-amide |
| 43 | Thiophene-2-carboxylic acid [3-(4-tert-butoxy-benzyl)-3-aza-bicyclo[3.1.0]hex-6-ylmethyl]-(3-fluoro-4-morpholin-4-yl-phenyl)-amide |
| 44 | Thiophene-2-carboxylic acid [3-(4-bromo-benzyl)-3-aza-bicyclo[3.1.0]hex-6-ylmethyl]-(3-fluoro-4-morpholin-4-yl-phenyl)-amide |
| 45 | Thiophene-2-carboxylic acid (3-fluoro-4-morpholin-4-yl-phenyl)-[3-(4-isopropyl-benzyl)-3-aza-bicyclo[3.1.0]hex-6-ylmethyl]-amide |
| 46 | Thiophene-2-carboxylic acid (3-biphenyl-4-ylmethyl-3-aza-bicyclo[3.1.0]hex-6-ylmethyl)-(3-fluoro-4-morpholin-4-yl-phenyl)-amide |
| 47 | Thiophene-2-carboxylic acid [3-(4-cyano-benzyl)-3-aza-bicyclo[3.1.0]hex-6-ylmethyl]-(3-fluoro-4-morpholin-4-yl-phenyl)-amide |
| 48 | Thiophene-2-carboxylic acid (3-fluoro-4-morpholin-4-yl-phenyl)-[3-(4-hydroxy-benzyl)-3-aza-bicyclo[3.1.0]hex-6-ylmethyl]-amide |
| 49 | Thiophene-2-carboxylic acid (3-fluoro-4-morpholin-4-yl-phenyl)-[3-(4-trifluoromethyl-benzyl)-3-aza-bicyclo[3.1.0]hex-6-ylmethyl]-amide |
| 50 | Thiophene-2-carboxylic acid [3-(4-ethoxy-benzyl)-3-aza-bicyclo[3.1.0]hex-6-ylmethyl]-(3-fluoro-4-morpholin-4-yl-phenyl)-amide |
| 51 | Thiophene-2-carboxylic acid (3-fluoro-4-morpholin-4-yl-phenyl)-[3-(4-methylsulfanyl-benzyl)-3-aza-bicyclo[3.1.0]hex-6-ylmethyl]-amide |
| 52 | Thiophene-2-carboxylic acid (3-fluoro-4-morpholin-4-yl-phenyl)-[3-(4-phenoxy-benzyl)-3-aza-bicyclo[3.1.0]hex-6-ylmethyl]-amide |
| 53 | 4-(6-{[(3-Fluoro-4-morpholin-4-yl-phenyl)-(thiophene-2-carbonyl)-amino]-methyl}-3-aza-bicyclo[3.1.0]hex-3-ylmethyl)-benzoic acid methyl ester |
| 54 | Thiophene-2-carboxylic acid [3-(4-tert-butyl-benzyl)-3-aza-bicyclo[3.1.0]hex-6-ylmethyl]-(3-fluoro-4-morpholin-4-yl-phenyl)-amide |
| 55 | Thiophene-2-carboxylic acid (3-fluoro-4-morpholin-4-yl-phenyl)-[3-(4-isobutyl-benzyl)-3-aza-bicyclo[3.1.0]hex-6-ylmethyl]-amide |
| 56 | Thiophene-2-carboxylic acid [3-(4-acetylamino-benzyl)-3-aza-bicyclo[3.1.0]hex-6-ylmethyl]-(3-fluoro-4-morpholin-4-yl-phenyl)-amide |
| 57 | Thiophene-2-carboxylic acid (3-fluoro-4-morpholin-4-yl-phenyl)-[3-(4-imidazol-1-yl-benzyl)-3-aza-bicyclo[3.1.0]hex-6-ylmethyl]-amide |
| 58 | Thiophene-2-carboxylic acid [3-(4-benzyloxy-benzyl)-3-aza-bicyclo[3.1.0]hex-6-ylmethyl]-(3-fluoro-4-morpholin-4-yl-phenyl)-amide |
| 59 | Thiophene-2-carboxylic acid (3-fluoro-4-morpholin-4-yl-phenyl)-[3-(4-pyridin-2-yl-benzyl)-3-aza-bicyclo[3.1.0]hex-6-ylmethyl]-amide |
| 60 | Thiophene-2-carboxylic acid (3-fluoro-4-morpholin-4-yl-phenyl)-[3-(4-morpholin-4-yl-benzyl)-3-aza-bicyclo[3.1.0]hex-6-ylmethyl]-amide |
| 61 | Thiophene-2-carboxylic acid (3-fluoro-4-morpholin-4-yl-phenyl)-[3-(4-pyrimidin-5-yl-benzyl)-3-aza-bicyclo[3.1.0]hex-6-ylmethyl]-amide |

-continued

| Compound ID | IUPAC NAME |
|---|---|
| 62 | Thiophene-2-carboxylic acid (3-fluoro-4-morpholin-4-yl-phenyl)-[3-(4,5,6,7-tetrahydro-benzothiazol-2-ylmethyl)-3-aza-bicyclo[3.1.0]hex-6-ylmethyl]-amide |
| 63 | Thiophene-2-carboxylic acid (3-fluoro-4-morpholin-4-yl-phenyl)-[3-(3-propoxy-benzyl)-3-aza-bicyclo[3.1.0]hex-6-ylmethyl]-amide |
| 64 | Thiophene-2-carboxylic acid (3-fluoro-4-morpholin-4-yl-phenyl)-[3-(3-phenyl-propyl)-3-aza-bicyclo[3.1.0]hex-6-ylmethyl]-amide |
| 65 | Thiophene-2-carboxylic acid [3-(5-ethyl-thiophen-2-ylmethyl)-3-aza-bicyclo[3.1.0]hex-6-ylmethyl]-(3-fluoro-4-morpholin-4-yl-phenyl)-amide |
| 66 | Thiophene-2-carboxylic acid [3-(3-ethoxy-benzyl)-3-aza-bicyclo[3.1.0]hex-6-ylmethyl]-(3-fluoro-4-morpholin-4-yl-phenyl)-amide |
| 67 | Thiophene-2-carboxylic acid (3-fluoro-4-morpholin-4-yl-phenyl)-[3-(4-propoxy-benzyl)-3-aza-bicyclo[3.1.0]hex-6-ylmethyl]-amide |
| 68 | Thiophene-2-carboxylic acid [3-(4-allyloxy-benzyl)-3-aza-bicyclo[3.1.0]hex-6-ylmethyl]-(3-fluoro-4-morpholin-4-yl-phenyl)-amide |
| 69 | Thiophene-2-carboxylic acid (3-fluoro-4-morpholin-4-yl-phenyl)-(3-hexyl-3-aza-bicyclo[3.1.0]hex-6-ylmethyl)-amide |
| 70 | Thiophene-2-carboxylic acid [3-(4-tert-butyl-benzyl)-3-aza-bicyclo[3.1.0]hex-6-ylmethyl]-(4-morpholin-4-yl-benzyl)-amide |
| 71 | Thiophene-2-carboxylic acid (4-tert-butyl-phenyl)-[3-(4-ethyl-benzyl)-3-aza-bicyclo[3.1.0]hex-6-ylmethyl]-amide |
| 72 | Thiophene-2-carboxylic acid [3-(4-ethyl-benzyl)-3-aza-bicyclo[3.1.0]hex-6-ylmethyl]-(4-piperidin-1-yl-phenyl)-amide |
| 73 | Thiophene-2-carboxylic acid (4-diethylamino-phenyl)-[3-(4-ethyl-benzyl)-3-aza-bicyclo[3.1.0]hex-6-ylmethyl]-amide |
| 74 | Thiophene-2-carboxylic acid [3-(4-ethyl-benzyl)-3-aza-bicyclo[3.1.0]hex-6-ylmethyl]-[4-(4-ethyl-2,6-dioxo-piperidin-4-yl)-phenyl]-amide |
| 75 | Thiophene-2-carboxylic acid (4-benzyl-phenyl)-[3-(4-ethyl-benzyl)-3-aza-bicyclo[3.1.0]hex-6-ylmethyl]-amide |
| 76 | Thiophene-2-carboxylic acid [3-(5-benzyl-pyridin-2-ylmethyl)-3-aza-bicyclo[3.1.0]hex-6-ylmethyl]-(3-fluoro-4-morpholin-4-yl-phenyl)-amide |
| 77 | Thiophene-2-carboxylic acid (3-fluoro-4-morpholin-4-yl-phenyl)-[3-(6-p-tolyloxy-pyridin-3-ylmethyl)-3-aza-bicyclo[3.1.0]hex-6-ylmethyl]-amide |
| 78 | Thiophene-2-carboxylic acid [3-(4-tert-butyl-cyclohexylmethyl)-3-aza-bicyclo[3.1.0]hex-6-ylmethyl]-(3-fluoro-4-morpholin-4-yl-phenyl)-amide |
| 79 | Thiophene-2-carboxylic acid {3-[2-fluoro-4-(1-hydroxy-1-methyl-ethyl)-benzyl]-3-aza-bicyclo[3.1.0]hex-6-ylmethyl}-(3-fluoro-4-morpholin-4-yl-phenyl)-amide |
| 80 | Thiophene-2-carboxylic acid [3-(4-tert-butyl-benzyl)-3-aza-bicyclo[3.1.0]hex-6-ylmethyl]-(6-morpholin-4-yl-pyridin-3-yl)-amide |
| 81 | Thiophene-2-carboxylic acid [3-(4-tert-butyl-benzyl)-3-aza-bicyclo[3.1.0]hex-6-ylmethyl]-{4-[ethyl-(2-hydroxy-ethyl)-amino]-phenyl}-amide |
| 82 | Thiophene-2-carboxylic acid [3-(4-tert-butyl-benzyl)-3-aza-bicyclo[3.1.0]hex-6-ylmethyl]-[4-(2-oxo-pyrrolidin-1-yl)-phenyl]-amide |
| 83 | Thiophene-2-carboxylic acid [3-(4-tert-butyl-benzyl)-3-aza-bicyclo[3.1.0]hex-6-ylmethyl]-[2-(2-ethoxy-ethyl)-1,2,3,4-tetrahydro-isoquinolin-7-yl]-amide |
| 84 | Thiophene-2-carboxylic acid [3-(4-tert-butyl-benzyl)-3-aza-bicyclo[3.1.0]hex-6-ylmethyl]-[4-(morpholine-4-carbonyl)-phenyl]-amide |

Example 2

Thiophene-2-carboxylic acid [3-(4-ethyl-benzoyl)-3-aza-bicyclo[3.1.0]hex-6-ylmethyl]-(3-fluoro-4-morpholin-4-yl-phenyl)-amide To a stirring solution of thiophene-2-carboxylic acid (3-aza-bicyclo[3.1.0]hex-6-ylmethyl)-(3-fluoro-4-morpholin-4-yl-phenyl)-amide (50 mg, 0.13 mmol) in 3 mL of anhydrous $CH_2Cl_2$, was added DIEA (0.065 mL, 0.37 mmol), followed by 4-ethylbenzoyl chloride (0.02 mL, 0.14 mmol). The reaction was stirred at room temperature for 1 hour, quenched with saturated $NaHCO_3$, and extracted with $CH_2Cl_2$. The combined extracts were dried over anhydrous $MgSO_4$, filtered and concentrated. The resulting crude material was purified via flash chromatography with 75% EtOAc/hexanes. The product containing fractions were collected and concentrated to yield 50 mg of a clear colorless oil. 400 MHz $^1$H NMR (CDCl$_3$) δ 7.25-7.28 (m, 3H), 7.14-7.16 (m, 2H), 6.82-6.92 (m, 4H), 6.76-6.78 (m, 1H), 4.02-4.09 (m, 1H), 3.84-3.91 (m, 5H), 3.48-3.54 (m, 2H), 3.37-3.44 (m, 2H), 3.08-3.11 (m, 4H), 2.60 (q, 2H), 1.45 (s, 2H), 1.16-1.19 (m, 3H), 0.82-0.85 (m, 1H); MS (M+1) 534.2.

General Procedure for the Acid Chloride Preparation of Compounds of Formula (VIII), where $R^{100}$ 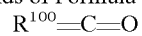 =O To a stirring solution of 1.0 equiv. of a compound of formula (VII) in methylene chloride (0.2 M) at room temperature was added DIEA (2.8 equiv.), followed by the acid chloride reagent of formula (IX) (1.1 equiv.). The reaction mixtures were stirred at room temperature for up to 24 hours. The mixtures were then quenched by the addition of saturated sodium bicarbonate solution and extracted with methylene chloride. The combined organic layers were dried over anhydrous $MgSO_4$ and concentrated under reduced pressure. The resulting crude material was purified by flash chromatography to yield the desired tertiary amines in 35-95% yield.

The following compounds were made using the above procedure of Example 2, starting with the appropriate starting amine of formula (VII) and the appropriate acid chloride reagent of formula (IX).

Furthermore, pharmaceutically acceptable salts of the compounds listed below can be prepared as follows. To a stirring solution of compounds of the general formula (VIII) (prepared as described above in Example 2, 1.0 equiv.) in a suitable solvent such as methyl ethyl ketone, methylene chloride/methanol (1:1) or methanol (0.1 M) at room temperature was added the appropriate acid, such as hydrochloric acid, citric acid, p-toluenesulfonic acid, methansulfonic acid or benzene sulfonic acid (1.0 equiv) in one portion. The resulting mixture was stirred at room temperature for up to 18 hours, during which time a precipitate formed. Filtration of the solid and drying under reduced pressure afforded the desired salts.

| Compound ID | IUPAC NAME |
|---|---|
| 85 | Thiophene-2-carboxylic acid {3-[4-(cyano-dimethyl-methyl)-benzoyl]-3-aza-bicyclo[3.1.0]hex-6-ylmethyl}-(3-fluoro-4-morpholin-4-yl-phenyl)-amide |
| 86 | Thiophene-2-carboxylic acid {3-[4-(cyano-dimethyl-methyl)-benzoyl]-3-aza-bicyclo[3.1.0]hex-6-ylmethyl}-(6-morpholin-4-yl-pyridin-3-yl)-amide |
| 87 | Thiophene-2-carboxylic acid [3-(4-tert-butyl-benzoyl)-3-aza-bicyclo[3.1.0]hex-6-ylmethyl]-[4-(tetrahydro-pyran-4-yl)-phenyl]-amide |
| 88 | Thiophene-2-carboxylic acid [3-(4-tert-butyl-benzoyl)-3-aza-bicyclo[3.1.0]hex-6-ylmethyl]-[4-(2-oxo-pyrrolidin-1-yl)-phenyl]-amide |
| 89 | Thiophene-2-carboxylic acid [3-(4-tert-butyl-benzoyl)-3-aza-bicyclo[3.1.0]hex-6-ylmethyl]-[2-(2-ethoxy-ethyl)-1,2,3,4-tetrahydro-isoquinolin-7-yl]-amide |
| 90 | 3-Chloro-thiophene-2-carboxylic acid [3-(4-tert-butyl-benzoyl)-3-aza-bicyclo[3.1.0]hex-6-ylmethyl]-(6-morpholin-4-yl-pyridin-3-yl)-amide |
| 91 | Thiophene-2-carboxylic acid [3-(4-tert-butyl-benzoyl)-3-aza-bicyclo[3.1.0]hex-6-ylmethyl]-[4-(morpholine-4-carbonyl)-phenyl]-amide |
| 92 | Thiophene-2-carboxylic acid [3-(4-tert-butyl-benzoyl)-3-aza-bicyclo[3.1.0]hex-6-ylmethyl]-(4-morpholin-4-ylmethyl-phenyl)-amide |
| 93 | Thiophene-2-carboxylic acid [3-(4-tert-butyl-benzoyl)-3-aza-bicyclo[3.1.0]hex-6-ylmethyl]-(6-thiomorpholin-4-yl-pyridin-3-yl)-amide |
| 94 | Thiophene-2-carboxylic acid [3-(4-tert-butyl-benzoyl)-3-aza-bicyclo[3.1.0]hex-6-ylmethyl]-(6-chloro-pyridin-3-yl)-amide |
| 95 | 5-Fluoro-thiophene-2-carboxylic acid [3-(4-tert-butyl-benzoyl)-3-aza-bicyclo[3.1.0]hex-6-ylmethyl]-(6-morpholin-4-yl-pyridin-3-yl)-amide |
| 96 | 5-Methyl-thiophene-2-carboxylic acid [3-(4-tert-butyl-benzoyl)-3-aza-bicyclo[3.1.0]hex-6-ylmethyl]-(6-morpholin-4-yl-pyridin-3-yl)-amide |
| 97 | Thiophene-2-carboxylic acid [3-(4-tert-butyl-benzoyl)-3-aza-bicyclo[3.1.0]hex-6-ylmethyl]-[1-(tetrahydro-pyran-4-yl)-pyrrolidin-3-yl]-amide |
| 98 | N-[3-(4-tert-Butyl-benzoyl)-3-aza-bicyclo[3.1.0]hex-6-ylmethyl]-4-methyl-N-(6-morpholin-4-yl-pyridin-3-yl)-benzamide |
| 99 | Thiophene-2-carboxylic acid [3-(4-tert-butyl-benzoyl)-3-aza-bicyclo[3.1.0]hex-6-ylmethyl]-[6-(3,6-dihydro-2H-pyran-4-yl)-pyridin-3-yl]-amide |
| 100 | Thiophene-2-carboxylic acid [3-(4-ethyl-benzoyl)-3-aza-bicyclo[3.1.0]hex-6-ylmethyl]-(3-fluoro-4-morpholin-4-yl-phenyl)-amide |
| 101 | Thiophene-2-carboxylic acid [3-(4-tert-butyl-benzoyl)-3-aza-bicyclo[3.1.0]hex-6-ylmethyl]-[6-(tetrahydro-pyran-4-yl)-pyridin-3-yl]-amide |
| 102 | Furan-2-carboxylic acid [3-(4-tert-butyl-benzoyl)-3-aza-bicyclo[3.1.0]hex-6-ylmethyl]-(6-morpholin-4-yl-pyridin-3-yl)-amide |
| 103 | 1-Methyl-1H-pyrrole-2-carboxylic acid [3-(4-tert-butyl-benzoyl)-3-aza-bicyclo[3.1.0]hex-6-ylmethyl]-(6-morpholin-4-yl-pyridin-3-yl)-amide |
| 104 | 4-Methyl-[1,2,3]thiadiazole-5-carboxylic acid [3-(4-tert-butyl-benzoyl)-3-aza-bicyclo[3.1.0]hex-6-ylmethyl]-(6-morpholin-4-yl-pyridin-3-yl)-amide |
| 105 | Pyridine-2-carboxylic acid [3-(4-tert-butyl-benzoyl)-3-aza-bicyclo[3.1.0]hex-6-ylmethyl]-(6-morpholin-4-yl-pyridin-3-yl)-amide |
| 106 | Benzofuran-2-carboxylic acid [3-(4-tert-butyl-benzoyl)-3-aza-bicyclo[3.1.0]hex-6-ylmethyl]-(6-morpholin-4-yl-pyridin-3-yl)-amide |
| 107 | 2-Methyl-thiazole-4-carboxylic acid [3-(4-tert-butyl-benzoyl)-3-aza-bicyclo[3.1.0]hex-6-ylmethyl]-(6-morpholin-4-yl-pyridin-3-yl)-amide |
| 108 | Thiophene-2-carboxylic acid [3-(4-tert-butyl-benzoyl)-3-aza-bicyclo[3.1.0]hex-6-ylmethyl]-(4-morpholin-4-yl-cyclohexyl)-amide |
| 109 | Thiophene-2-carboxylic acid [3-(4-tert-butyl-benzoyl)-3-aza-bicyclo[3.1.0]hex-6-ylmethyl]-(4-morpholin-4-yl-cyclohexyl)-amide |
| 110 | Thiophene-2-carboxylic acid [3-(4-tert-butyl-benzoyl)-3-aza-bicyclo[3.1.0]hex-6-ylmethyl]-(6-morpholin-4-ylmethyl-pyridin-3-yl)-amide |
| 111 | Thiophene-2-carboxylic acid [3-(4-tert-butyl-benzoyl)-3-aza-bicyclo[3.1.0]hex-6-ylmethyl]-(3-fluoro-4-morpholin-4-yl-phenyl)-amide |
| 112 | Thiophene-2-carboxylic acid [3-(5-butyl-pyridine-2-carbonyl)-3-aza-bicyclo[3.1.0]hex-6-ylmethyl]-(3-fluoro-4-morpholin-4-yl-phenyl)-amide |
| 113 | Thiophene-2-carboxylic acid [3-(4-tert-butyl-cyclohexanecarbonyl)-3-aza-bicyclo[3.1.0]hex-6-ylmethyl]-(3-fluoro-4-morpholin-4-yl-phenyl)-amide |
| 114 | Thiophene-2-carboxylic acid {3-[2-(4-tert-butyl-phenyl)-acetyl]-3-aza-bicyclo[3.1.0]hex-6-ylmethyl}-(3-fluoro-4-morpholin-4-yl-phenyl)-amide |

-continued

| Compound ID | IUPAC NAME |
|---|---|
| 115 | Thiophene-2-carboxylic acid [3-(4-tert-butyl-benzoyl)-3-aza-bicyclo[3.1.0]hex-6-ylmethyl]-(6-morpholin-4-yl-pyridin-3-yl)-amide |
| 116 | Thiophene-2-carboxylic acid [3-(4-tert-butyl-benzoyl)-3-aza-bicyclo[3.1.0]hex-6-ylmethyl]-(4-diethylcarbamoyl-phenyl)-amide |
| 117 | Thiophene-2-carboxylic acid [3-(4-tert-butyl-benzoyl)-3-aza-bicyclo[3.1.0]hex-6-ylmethyl]-[1-(tetrahydro-pyran-4-yl)-piperidin-4-yl]-amide |
| 118 | 3-Chloro-thiophene-2-carboxylic acid [3-(4-tert-butyl-benzoyl)-3-aza-bicyclo[3.1.0]hex-6-ylmethyl]-(3-fluoro-4-morpholin-4-yl-phenyl)-amide |
| 119 | Thiophene-2-carboxylic acid [3-(4-tert-butyl-benzoyl)-3-aza-bicyclo[3.1.0]hex-6-ylmethyl]-[3-(tetrahydro-pyran-4-yl)-3-aza-bicyclo[3.1.0]hex-6-yl]-amide |
| 120 | N-[3-(4-tert-Butyl-benzoyl)-3-aza-bicyclo[3.1.0]hex-6-ylmethyl]-6-morpholin-4-yl-N-thiophen-2-ylmethyl-nicotinamide |

Example 3

Thiophene-2-carboxylic acid [3-(4-tert-butyl-benzenesulfonyl)-3-aza-bicyclo[3.1.0]hex-6yl-methyl]-(3-fluoro-4-morpholin-4-yl-phenyl)-amide To a stirring solution of thiophene-2-carboxylic acid (3-aza-bicyclo[3.1.0]hex-6-ylmethyl)-(3-fluoro-4-morpholin-4-yl-phenyl)-amide (60 mg, 0.15 mmol) in 3 mL of DCE was added DIEA (0.026 mL, 0.45 mmol), DMAP (cat.) and 4-tert-butylbenzene sulfonyl chloride (0.10 mL, 0.45 mmol). The resulting mixture was heated to 80° C. for 1.5 hours, cooled to room temperature and quenched with saturated NaHCO$_3$. The layers were separated, the aqueous layer was extracted with CH$_2$Cl$_2$, and the combined organic layers were dried and concentrated. The resulting crude material was purified via flash chromatography with 40% EtOAc/hexanes. The product containing fractions were collected and concentrated to yield 70 mg of a white foam. 400 MHz $^1$H NMR (CDCl$_3$) δ 7.62-7.66 (m, 2H), 7.47-7.50 (m, 2H), 7.29-7.31 (m, 1H), 6.79-6.95 (m, 5H), 3.87-3.89 (m, 4H), 3.68 (d, J=7.47 Hz, 2H), 3.46 (d, J=9.13 Hz, 2H), 3.13-3.15 (m, 4H), 2.94-2.96 (m, 2H), 1.64 (s, 2H), 1.31 (s, 9H), 1.12-1.14 (m, 1H); MS (M+1) 598.2.

General Procedure for the Sulfonyl Chloride Preparations of Compounds of Formula (VIII), Where R$^{100}$=SO$_2$ To a stirring solution of 1.0 equiv. of a compound of formula (VII) in DCE (0.2 M) at room temperature was added DIEA (3.0 equiv.), followed by the sulfonyl chloride reagent of formula (IX) (3.0 equiv.). The reaction mixtures were heated at 80° C. for up to 18 hours. The mixtures were then cooled to room temperature, quenched by the addition of saturated sodium bicarbonate solution and extracted with methylene chloride. The combined organic layers were dried over anhydrous MgSO$_4$ and concentrated under reduced pressure. The resulting crude material was purified by flash chromatography to yield the desired tertiary amines in 55-95% yield.

The following compounds were made using the above procedure of Example 3, starting with the appropriate starting amine of formula (VII) and the appropriate sulfonyl chloride reagent of formula (IX).

Furthermore, pharmaceutically acceptable salts of the compounds listed below can be prepared as follows. To a stirring solution of compounds of the general formula (VIII) (prepared as described above in Example 3, 1.0 equiv.) in a suitable solvent such as methyl ethyl ketone, methylene chloride/methanol (1:1) or methanol (0.1 M) at room temperature was added the appropriate acid, such as hydrochloric acid, citric acid, p-toluenesulfonic acid, methansulfonic acid or benzene sulfonic acid (1.0 equiv) in one portion. The resulting mixture was stirred at room temperature for up to 18 hours, during which time a precipitate formed. Filtration of the solid and drying under reduced pressure afforded the desired salts.

| Compound ID | IUPAC NAME |
|---|---|
| 121 | Thiophene-2-carboxylic acid (3-fluoro-4-morpholin-4-yl-phenyl)-[3-(3-trifluoromethyl-phenylmethanesulfonyl)-3-aza-bicyclo[3.1.0]hex-6-ylmethyl]-amide |
| 122 | Thiophene-2-carboxylic acid {3-[3-(4-chloro-phenoxy)-benzenesulfonyl]-3-aza-bicyclo[3.1.0]hex-6-ylmethyl}-(3-fluoro-4-morpholin-4-yl-phenyl)-amide |
| 123 | Thiophene-2-carboxylic acid (3-fluoro-4-morpholin-4-yl-phenyl)-[3-(4-trifluoromethoxy-benzenesulfonyl)-3-aza-bicyclo[3.1.0]hex-6-ylmethyl]-amide |
| 124 | Thiophene-2-carboxylic acid [3-(4-cyano-benzenesulfonyl)-3-aza-bicyclo[3.1.0]hex-6-ylmethyl]-(3-fluoro-4-morpholin-4-yl-phenyl)-amide |
| 125 | Thiophene-2-carboxylic acid (3-fluoro-4-morpholin-4-yl-phenyl)-{3-[4-(pyridin-2-yloxy)-benzenesulfonyl]-3-aza-bicyclo[3.1.0]hex-6-ylmethyl}-amide |

-continued

| Compound ID | IUPAC NAME |
|---|---|
| 126 | Thiophene-2-carboxylic acid [3-(4-butyl-benzenesulfonyl)-3-aza-bicyclo[3.1.0]hex-6-ylmethyl]-(3-fluoro-4-morpholin-4-yl-phenyl)-amide |
| 127 | Thiophene-2-carboxylic acid (3-fluoro-4-morpholin-4-yl-phenyl)-{3-[4-(pyridin-3-yloxy)-benzenesulfonyl]-3-aza-bicyclo[3.1.0]hex-6-ylmethyl}-amide |
| 128 | Thiophene-2-carboxylic acid (3-fluoro-4-morpholin-4-yl-phenyl)-[3-(toluene-4-sulfonyl)-3-aza-bicyclo[3.1.0]hex-6-ylmethyl]-amide |
| 129 | Thiophene-2-carboxylic acid {3-[4-(4-chloro-phenoxy)-benzenesulfonyl]-3-aza-bicyclo[3.1.0]hex-6-ylmethyl}-(3-fluoro-4-morpholin-4-yl-phenyl)-amide |
| 130 | Thiophene-2-carboxylic acid [3-(4'-fluoro-biphenyl-4-sulfonyl)-3-aza-bicyclo[3.1.0]hex-6-ylmethyl]-(3-fluoro-4-morpholin-4-yl-phenyl)-amide |
| 131 | Thiophene-2-carboxylic acid (3-fluoro-4-morpholin-4-yl-phenyl)-[3-(1-methyl-1H-imidazole-4-sulfonyl)-3-aza-bicyclo[3.1.0]hex-6-ylmethyl]-amide |
| 132 | Thiophene-2-carboxylic acid [3-(4-bromo-benzenesulfonyl)-3-aza-bicyclo[3.1.0]hex-6-ylmethyl]-(3-fluoro-4-morpholin-4-yl-phenyl)-amide |
| 133 | Thiophene-2-carboxylic acid [3-(4-bromo-benzenesulfonyl)-3-aza-bicyclo[3.1.0]hex-6-ylmethyl]-(3-fluoro-4-morpholin-4-yl-phenyl)-amide |
| 134 | Thiophene-2-carboxylic acid [3-(2-acetylamino-4-methyl-thiazole-5-sulfonyl)-3-aza-bicyclo[3.1.0]hex-6-ylmethyl]-(3-fluoro-4-morpholin-4-yl-phenyl)-amide |
| 135 | Thiophene-2-carboxylic acid [3-(4-tert-butyl-benzenesulfonyl)-3-aza-bicyclo[3.1.0]hex-6-ylmethyl]-(4-diethylcarbamoyl-phenyl)-amide |
| 136 | Thiophene-2-carboxylic acid (3-fluoro-4-morpholin-4-yl-phenyl)-[3-(4-methyl-thiophene-2-sulfonyl)-3-aza-bicyclo[3.1.0]hex-6-ylmethyl]-amide |
| 137 | Thiophene-2-carboxylic acid [3-(4-chloro-benzenesulfonyl)-3-aza-bicyclo[3.1.0]hex-6-ylmethyl]-(3-fluoro-4-morpholin-4-yl-phenyl)-amide |
| 138 | 3-Chloro-thiophene-2-carboxylic acid [3-(4-tert-butyl-benzenesulfonyl)-3-aza-bicyclo[3.1.0]hex-6-ylmethyl]-(3-fluoro-4-morpholin-4-yl-phenyl)-amide |
| 139 | Thiophene-2-carboxylic acid [3-(4-fluoro-benzenesulfonyl)-3-aza-bicyclo[3.1.0]hex-6-ylmethyl]-(3-fluoro-4-morpholin-4-yl-phenyl)-amide |
| 140 | Thiophene-2-carboxylic acid [3-(4-tert-butyl-benzenesulfonyl)-3-aza-bicyclo[3.1.0]hex-6-ylmethyl]-[4-(2-oxo-pyrrolidin-1-yl)-phenyl]-amide |
| 141 | Thiophene-2-carboxylic acid [3-(benzo[b]thiophene-2-sulfonyl)-3-aza-bicyclo[3.1.0]hex-6-ylmethyl]-(3-fluoro-4-morpholin-4-yl-phenyl)-amide |
| 142 | Thiophene-2-carboxylic acid [3-(biphenyl-3-sulfonyl)-3-aza-bicyclo[3.1.0]hex-6-ylmethyl]-(3-fluoro-4-morpholin-4-yl-phenyl)-amide |
| 143 | Thiophene-2-carboxylic acid [3-(4-tert-butyl-benzenesulfonyl)-3-aza-bicyclo[3.1.0]hex-6-ylmethyl]-[2-(2-ethoxy-ethyl)-1,2,3,4-tetrahydro-isoquinolin-7-yl]-amide |
| 144 | Thiophene-2-carboxylic acid (3-fluoro-4-morpholin-4-yl-phenyl)-(3-phenylmethanesulfonyl-3-aza-bicyclo[3.1.0]hex-6-ylmethyl)-amide |
| 145 | 3-Chloro-thiophene-2-carboxylic acid [3-(4-tert-butyl-benzenesulfonyl)-3-aza-bicyclo[3.1.0]hex-6-ylmethyl]-(6-morpholin-4-yl-pyridin-3-yl)-amide |
| 146 | Thiophene-2-carboxylic acid [3-(4-chloro-phenylmethanesulfonyl)-3-aza-bicyclo[3.1.0]hex-6-ylmethyl]-(3-fluoro-4-morpholin-4-yl-phenyl)-amide |
| 147 | 5-Fluoro-thiophene-2-carboxylic acid [3-(4-tert-butyl-benzenesulfonyl)-3-aza-bicyclo[3.1.0]hex-6-ylmethyl]-(6-morpholin-4-yl-pyridin-3-yl)-amide |
| 148 | Thiophene-2-carboxylic acid [3-(4-tert-butyl-benzenesulfonyl)-3-aza-bicyclo[3.1.0]hex-6-ylmethyl]-[4-(morpholine-4-carbonyl)-phenyl]-amide |
| 149 | 4-Methyl-[1,2,3]thiadiazole-5-carboxylic acid [3-(4-tert-butyl-benzenesulfonyl)-3-aza-bicyclo[3.1.0]hex-6-ylmethyl]-(6-morpholin-4-yl-pyridin-3-yl)-amide |
| 150 | 1-Methyl-1H-pyrrole-2-carboxylic acid [3-(4-tert-butyl-benzenesulfonyl)-3-aza-bicyclo[3.1.0]hex-6-ylmethyl]-(6-morpholin-4-yl-pyridin-3-yl)-amide |
| 151 | Thiophene-2-carboxylic acid (3-fluoro-4-morpholin-4-yl-phenyl)-[3-(quinoline-8-sulfonyl)-3-aza-bicyclo[3.1.0]hex-6-ylmethyl]-amide |
| 152 | Thiophene-2-carboxylic acid (3-fluoro-4-morpholin-4-yl-phenyl)-[3-(4-propyl-benzenesulfonyl)-3-aza-bicyclo[3.1.0]hex-6-ylmethyl]-amide |
| 153 | Thiophene-2-carboxylic acid (3-fluoro-4-morpholin-4-yl-phenyl)-[3-(4-methoxy-benzenesulfonyl)-3-aza-bicyclo[3.1.0]hex-6-ylmethyl]-amide |
| 154 | Thiophene-2-carboxylic acid (3-fluoro-4-morpholin-4-yl-phenyl)-[3-(2-methoxy-4-methyl-benzenesulfonyl)-3-aza-bicyclo[3.1.0]hex-6-ylmethyl]-amide |
| 155 | Thiophene-2-carboxylic acid (3-fluoro-4-morpholin-4-yl-phenyl)-[3-(4-trifluoromethyl-benzenesulfonyl)-3-aza-bicyclo[3.1.0]hex-6-ylmethyl]-amide |
| 156 | Thiophene-2-carboxylic acid (3-fluoro-4-morpholin-4-yl-phenyl)-[3-(isoquinoline-5-sulfonyl)-3-aza-bicyclo[3.1.0]hex-6-ylmethyl]-amide |
| 157 | Thiophene-2-carboxylic acid (3-fluoro-4-morpholin-4-yl-phenyl)-[3-(4-isopropyl-benzenesulfonyl)-3-aza-bicyclo[3.1.0]hex-6-ylmethyl]-amide |
| 158 | Thiophene-2-carboxylic acid [3-(5-bromo-6-chloro-pyridine-3-sulfonyl)-3-aza-bicyclo[3.1.0]hex-6-ylmethyl]-(3-fluoro-4-morpholin-4-yl-phenyl)-amide |

-continued

| Compound ID | IUPAC NAME |
|---|---|
| 159 | Thiophene-2-carboxylic acid [3-(4-ethyl-benzenesulfonyl)-3-aza-bicyclo[3.1.0]hex-6-ylmethyl]-(3-fluoro-4-morpholin-4-yl-phenyl)-amide |
| 160 | Thiophene-2-carboxylic acid (3-fluoro-4-morpholin-4-yl-phenyl)-[3-(2-oxo-2H-chromene-6-sulfonyl)-3-aza-bicyclo[3.1.0]hex-6-ylmethyl]-amide |
| 161 | Thiophene-2-carboxylic acid (3-fluoro-4-morpholin-4-yl-phenyl)-[3-(4-fluoro-phenylmethanesulfonyl)-3-aza-bicyclo[3.1.0]hex-6-ylmethyl]-amide |
| 162 | Thiophene-2-carboxylic acid (3-fluoro-4-morpholin-4-yl-phenyl)-[3-(4-nitro-benzenesulfonyl)-3-aza-bicyclo[3.1.0]hex-6-ylmethyl]-amide |
| 163 | Thiophene-2-carboxylic acid (3-fluoro-4-morpholin-4-yl-phenyl)-[3-(4-trifluoromethyl-phenylmethanesulfonyl)-3-aza-bicyclo[3.1.0]hex-6-ylmethyl]-amide |
| 164 | Thiophene-2-carboxylic acid (3-fluoro-4-morpholin-4-yl-phenyl)-{3-[4-(pyridin-4-yloxy)-benzenesulfonyl]-3-aza-bicyclo[3.1.0]hex-6-ylmethyl}-amide |
| 165 | 4-(6-{[(3-Fluoro-4-morpholin-4-yl-phenyl)-(thiophene-2-carbonyl)-amino]-methyl}-3-aza-bicyclo[3.1.0]hexane-3-sulfonyl)-benzoic acid |
| 166 | Thiophene-2-carboxylic acid [3-(biphenyl-4-sulfonyl)-3-aza-bicyclo[3.1.0]hex-6-ylmethyl]-(3-fluoro-4-morpholin-4-yl-phenyl)-amide |
| 167 | Thiophene-2-carboxylic acid [3-(4-butoxy-benzenesulfonyl)-3-aza-bicyclo[3.1.0]hex-6-ylmethyl]-(3-fluoro-4-morpholin-4-yl-phenyl)-amide |
| 168 | Thiophene-2-carboxylic acid [3-(4'-chloro-biphenyl-3-sulfonyl)-3-aza-bicyclo[3.1.0]hex-6-ylmethyl]-(3-fluoro-4-morpholin-4-yl-phenyl)-amide |
| 169 | Thiophene-2-carboxylic acid [3-(4-acetyl-benzenesulfonyl)-3-aza-bicyclo[3.1.0]hex-6-ylmethyl]-(3-fluoro-4-morpholin-4-yl-phenyl)-amide |
| 170 | Cyclopropanecarboxylic acid [3-(4-tert-butyl-benzenesulfonyl)-3-aza-bicyclo[3.1.0]hex-6-ylmethyl]-(6-morpholin-4-yl-pyridin-3-yl)-amide |
| 171 | Thiophene-2-carboxylic acid (3-fluoro-4-morpholin-4-yl-phenyl)-[3-(4-pentyl-benzenesulfonyl)-3-aza-bicyclo[3.1.0]hex-6-ylmethyl]-amide |
| 172 | Cyclopentanecarboxylic acid [3-(4-tert-butyl-benzenesulfonyl)-3-aza-bicyclo[3.1.0]hex-6-ylmethyl]-(6-morpholin-4-yl-pyridin-3-yl)-amide |
| 173 | Thiophene-2-carboxylic acid (3-fluoro-4-morpholin-4-yl-phenyl)-[3-(4-phenoxy-benzenesulfonyl)-3-aza-bicyclo[3.1.0]hex-6-ylmethyl]-amide |
| 174 | Cyclobutanecarboxylic acid [3-(4-tert-butyl-benzenesulfonyl)-3-aza-bicyclo[3.1.0]hex-6-ylmethyl]-(6-morpholin-4-yl-pyridin-3-yl)-amide |
| 175 | 3-[4-(6-{[(3-Fluoro-4-morpholin-4-yl-phenyl)-(thiophene-2-carbonyl)-amino]-methyl}-3-aza-bicyclo[3.1.0]hexane-3-sulfonyl)-phenyl]-propionic acid methyl ester |
| 176 | Thiophene-2-carboxylic acid [3-(4-acetylamino-benzenesulfonyl)-3-aza-bicyclo[3.1.0]hex-6-ylmethyl]-(3-fluoro-4-morpholin-4-yl-phenyl)-amide |
| 177 | N-[3-(4-tert-Butyl-benzenesulfonyl)-3-aza-bicyclo[3.1.0]hex-6-ylmethyl]-4-methyl-N-(6-morpholin-4-yl-pyridin-3-yl)-benzamide |
| 178 | Thiophene-2-carboxylic acid {3-[4-(1,1-dimethyl-propyl)-benzenesulfonyl]-3-aza-bicyclo[3.1.0]hex-6-ylmethyl}-(3-fluoro-4-morpholin-4-yl-phenyl)-amide |
| 179 | Thiophene-2-carboxylic acid (3-fluoro-4-morpholin-4-yl-phenyl)-[3-(naphthalene-2-sulfonyl)-3-aza-bicyclo[3.1.0]hex-6-ylmethyl]-amide |
| 180 | Thiophene-2-carboxylic acid [3-(4-tert-butyl-benzenesulfonyl)-3-aza-bicyclo[3.1.0]hex-6-ylmethyl]-(6-morpholin-4-yl-pyridin-3-yl)-amide |

Preparation 5

[3-(4-Ethyl-benzyl)-3-aza-bicyclo[3.1.0]hex-6-yl]-methanol

To a stirring solution of (3-Aza-bicyclo[3.1.0]hex-6-yl)-methanol (18.4 gm, 123 mmol) in 450 mL of MeOH at room temperature was added 4-ethylbenzaldehyde (18.5 mL, 135 mmol) and NaCNBH$_3$ (8.5 gm, 135 mmol). After stirring 3 hours, the reaction mixture was concentrated under reduce pressure, taken up in water, treated with 1 M NaOH, and diluted with CH$_2$Cl$_2$. The layers were separated, the aqueous layer was extracted with CH$_2$Cl$_2$ and the combined organic layers were dried and concentrated under reduced pressure. The crude material was dissolved in CH$_2$Cl$_2$, treated with 1 M HCl and concentrated. This material was taken up in water and extracted with Et$_2$O, the aqueous layer was basified with NH$_4$OH and extracted with CH$_2$Cl$_2$. The combined extracts were dried, filtered and concentrated under reduce pressure to yield 22.4 gm of the desired amine. 400 MHz $^1$H NMR (CDCl$_3$) δ 7.14-7.16 (m, 2H), 7.08-7.10 (m, 2H), 3.54 (s, 2H), 3.38-3.40 (m, 2H), 2.95 (d, J=8.7 Hz, 2H), 2.59 (q, 2H), 2.33 (d, J=8.7 Hz, 2H), 1.55-1.59 (m, 1H),1.42 (brs, 1H), 1.25-1.26 (m, 2H), 1.18-1.23 (m, 3H); MS (M+1) 232.2.

Preparation 6

[3-(4-Ethyl-benzyl)-3-aza-bicyclo[3.1.0]hex-6-ylmethyl]-(3-fluoro-4-morpholin-4-yl-phenyl)-amine To a stirring solution of oxalyl chloride (0.45 mL, 5.19 mmol) in 25 mL of anhydrous CH$_2$Cl$_2$ at −78° C. was added DMSO (0.79 mL, 11.2 mmol) dropwise. After 10 minutes [3-(4-Ethyl-benzyl)-3-aza-bicyclo[3.1.0]hex-6-yl]-methanol (1.0 gm, 4.32 mmol) in 10 mL anhydrous CH$_2$Cl$_2$ was added. After the mixture stirred 30 minutes, triethylamine (3.01 mL, 21.6 mmol) was added and the mixture was allowed to slowly warm to 0° C. over 1 hour. The mixture was concentrated, the resulting solid was taken up in saturated NaHCO$_3$ and EtOAc, the layers were separated and the aqueous layer was extracted with EtOAc. The combined organic layers were dried, filtered and concentrated to yield the crude aldehyde, which was used in the next step without purification.

To a stirring solution of the crude aldehyde (1.32 gm, 5.75 mmol) in 40 mL of MeOH was added 3-fluoro4-morpholinoaniline (1.1 gm, 5.75 mmol), AcOH (0.46 mL, 8.05 mmol) and NaCNBH$_3$ (361 mg, 5.75 mmol). The reaction mixture was stirred at room temperature for 60 minutes. The mixture was concentrated under reduced pressure and the resulting material was taken up in saturated NaHCO$_3$ and extracted with CH$_2$Cl$_2$. The combined organic layers were dried over anhydrous MgSO$_4$, filtered and concentrated under reduced pressure. The resulting crude material was purified by flash chromatography with 10-25% iso-propanol/hexanes gradient. The product containing fractions were collected and concentrated to yield 1.55 gm of the desired amine. 400 MHz $^1$H NMR (CDCl$_3$) δ 7.18-7.20 (m, 2H), 7.12-7.14 (m, 2H), 6.80-6.84 (m, 1H), 6.29-6.35 (m, 2H), 3.84-3.86 (m, 4H), 3.62 (brs, 1H), 3.53-3.57 (m, 2H), 3.00 (d, J=8.70 Hz, 2H), 2.95-2.97 (m, 4H), 2.85 (d, J=7.05 Hz, 2H), 2.63 (q, 2H), 2.38 (d, J=8.40 Hz, 2H), 1.59 (s, 1H), 1.26-1.30 (m,2H), 1.23 (t, 3H); MS (M+1) 410.2.

The following compounds were made using the above procedure of Preparation 6.

(4-Bromo-3-fluoro-phenyl)-[3-(4ethyl-benzyl)-3-aza-bicyclo[3.1.0]hex-6-ylmethyl]-amine 400 MHz $^1$H NMR (CDCl$_3$) δ 7.13-7.23 (m, 4H), 6.27-6.38 (m, 2H), 6.20-6.22 (m, 1H), 3.58 (s, 2H), 3.01 (d, J=8.70 Hz, 2H), 2.82 (d, J=7.05 Hz, 2H), 2.62 (q, 2H), 2.39 (d, J=8.70 Hz, 2H), 1.53-1.57 (m, 1H), 1.29 (s, 2H), 1.23 (t, 3H); MS (M+1) 405.0.

Example 4

Benzo[b]thiophene-2-carboxylic acid [3-(4-ethyl-benzyl)-3-aza-bicyclo[3.1.0]hex-6-ylmethyl]-(3-fluoro-4-morpholin-yl-phenyl)-amide To a stirring solution of [3-(4-Ethyl-benzyl)-3-aza-bicyclo[3.1.0]hex-6-ylmethyl]-(3-fluoro-4-morpholin-4-yl-phenyl)-amine prepared above (50 mg, 0.12 mmol) in 2 mL of DCE at room temperature was added DIEA (0.03 mL, 0.18 mmol) and 2-benzthiophenecarbonylchloride (0.02 mL, 0.18 mmol). After 1 hour, saturated NaHCO$_3$ was added, and the mixture was extracted with CH$_2$Cl$_2$. The combined extracts were dried over anhydrous MgSO$_4$, filtered and concentrated under reduced pressure. The resulting crude material was taken up in 50% EtOAc/hexanes and the white solids were filtered off. The remaining filtrate was concentrated under reduce pressure to yield 58 mg of the desired product. 400 MHz $^1$H NMR (CDCl$_3$) δ 7.60-7.68 (m, 2H), 7.24-7.31 (m, 2H),7.08-7.18 (m, 5H), 6.99-7.02 (m, 2H), 6.86-6.91 (m, 1H), 3.82-3.88 (m, 4H), 3.68 (d, J=7.47 Hz, 2H), 3.50 (brs, 2H), 3.10-3.12 (m, 4H), 2.88 (brd, J=7.47 Hz, 2H), 2.49 (q, 2H), 2.28, (brs, 2H), 1.49 (brs, 1H), 1.22-1.24 (m, 2H), 1.19 (t, 3H); MS (M+1) 570.2.

The following compounds were made using the above procedure of Example 4, starting with the appropriate starting amine of formula (X) and the acid chloride reagent of formula (XI).

Furthermore, pharmaceutically acetable salts of the compounds listed below can be prepared as follows. To a stirring solution of compounds of the general formula (XII) (prepared as described above in Example 4, 1.0 equiv.) in a suitable solvent such as methyl ethyl ketone, methylene chloride/methanol (1:1) or methanol (0.1 M) at room temperature was added the appropriate acid, such as hydrochloric acid, citric acid, p-toluenesulfonic acid, methansulfonic acid or benzene sulfonic acid (1.0 equiv) in one portion. The resulting mixture was stirred at room temperature for up to 18 hours, during which time a precipitate formed. Filtration of the solid and drying under reduced pressure afforded the desired salts.

Thiophene-2-carboxylic acid (4-bromo-3-fluoro-phenyl)-[3-(4-ethyl-benzyl)-3-aza-bicyclo[3.1.0]hex-6-ylmethyl]-amide 400 MHz $^1$H NMR (CDCl$_3$) δ 7.54 (t, 1H), 7.31-7.32 (m, 1H), 7.04-7.12 (m, 5H), 6.93-9.95 (m, 1H), 6.80-6.84 (m, 2H), 3.67 (d, J=7.47 Hz, 2H), 3.49 (s, 2H), 2.85 (d, J=8.71 Hz, 2H), 2.59 (q, 2H), 2.25 (d, J=8.31 Hz, 2H), 1.46 (brs, 1H), 1.18-1.24 (m, 5H); MS (M+1) 513.0, 514.8.

| Compound ID | IUPAC NAME |
|---|---|
| 181 | N-[3-(4-Ethyl-benzyl)-3-aza-bicyclo[3.1.0]hex-6-ylmethyl]-N-(3-fluoro-4-morpholin-4-yl-phenyl)-isonicotinamide |
| 182 | Benzofuran-2-carboxylic acid [3-(4-ethyl-benzyl)-3-aza-bicyclo[3.1.0]hex-6-ylmethyl]-(3-fluoro-4-morpholin-4-yl-phenyl)-amide |
| 183 | Furan-3-carboxylic acid [3-(4-ethyl-benzyl)-3-aza-bicyclo[3.1.0]hex-6-ylmethyl]-(3-fluoro-4-morpholin-4-yl-phenyl)-amide |
| 184 | N-{1-[[3-(4-Ethyl-benzyl)-3-aza-bicyclo[3.1.0]hex-6-ylmethyl]-(3-fluoro-4-morpholin-4-yl-phenyl)-carbamoyl]-ethyl}-benzamide |
| 185 | 3-Bromo-thiophene-2-carboxylic acid [3-(4-ethyl-benzyl)-3-aza-bicyclo[3.1.0]hex-6-ylmethyl]-(3-fluoro-4-morpholin-4-yl-phenyl)-amide |
| 186 | 3-Methyl-furan-2-carboxylic acid [3-(4-ethyl-benzyl)-3-aza-bicyclo[3.1.0]hex-6-ylmethyl]-(3-fluoro-4-morpholin-4-yl-phenyl)-amide |
| 187 | 5-Methyl-isoxazole-3-carboxylic acid [3-(4-ethyl-benzyl)-3-aza-bicyclo[3.1.0]hex-6-ylmethyl]-(3-fluoro-4-morpholin-4-yl-phenyl)-amide |
| 188 | N-[3-(4-Ethyl-benzyl)-3-aza-bicyclo[3.1.0]hex-6-ylmethyl]-N-(3-fluoro-4-morpholin-4-yl-phenyl)-2-methoxy-benzamide |
| 189 | 3-Methyl-thiophene-2-carboxylic acid [3-(4-ethyl-benzyl)-3-aza-bicyclo[3.1.0]hex-6-ylmethyl]-(3-fluoro-4-morpholin-4-yl-phenyl)-amide |
| 190 | N-[3-(4-Ethyl-benzyl)-3-aza-bicyclo[3.1.0]hex-6-ylmethyl]-N-(3-fluoro-4-morpholin-4-yl-phenyl)-4-methoxy-benzamide |
| 191 | 2,5-Dimethyl-furan-3-carboxylic acid [3-(4-ethyl-benzyl)-3-aza-bicyclo[3.1.0]hex-6-ylmethyl]-(3-fluoro-4-morpholin-4-yl-phenyl)-amide |
| 192 | N-[3-(4-Ethyl-benzyl)-3-aza-bicyclo[3.1.0]hex-6-ylmethyl]-N-(3-fluoro-4-morpholin-4-yl-phenyl)-4-methyl-benzamide |

-continued

| Compound ID | IUPAC NAME |
|---|---|
| 193 | 5-Methyl-thiophene-2-carboxylic acid [3-(4-ethyl-benzyl)-3-aza-bicyclo[3.1.0]hex-6-ylmethyl]-(3-fluoro-4-morpholin-4-yl-phenyl)-amide |
| 194 | 5-tert-Butyl-2-methyl-2H-pyrazole-3-carboxylic acid [3-(4-ethyl-benzyl)-3-aza-bicyclo[3.1.0]hex-6-ylmethyl]-(3-fluoro-4-morpholin-4-yl-phenyl)-amide |
| 195 | N-[3-(4-Ethyl-benzyl)-3-aza-bicyclo[3.1.0]hex-6-ylmethyl]-N-(3-fluoro-4-morpholin-4-yl-phenyl)-3,5-dimethoxy-benzamide |
| 196 | N-[3-(4-Ethyl-benzyl)-3-aza-bicyclo[3.1.0]hex-6-ylmethyl]-N-(3-fluoro-4-morpholin-4-yl-phenyl)-3-methoxy-benzamide |
| 197 | 1,5-Dimethyl-1H-pyrazole-3-carboxylic acid [3-(4-ethyl-benzyl)-3-aza-bicyclo[3.1.0]hex-6-ylmethyl]-(3-fluoro-4-morpholin-4-yl-phenyl)-amide |
| 198 | 3-Ethoxy-thiophene-2-carboxylic acid [3-(4-ethyl-benzyl)-3-aza-bicyclo[3.1.0]hex-6-ylmethyl]-(3-fluoro-4-morpholin-4-yl-phenyl)-amide |
| 199 | Isoxazole-5-carboxylic acid [3-(4-ethyl-benzyl)-3-aza-bicyclo[3.1.0]hex-6-ylmethyl]-(3-fluoro-4-morpholin-4-yl-phenyl)-amide |
| 200 | 1-Methyl-1H-imidazole-2-carboxylic acid [3-(4-ethyl-benzyl)-3-aza-bicyclo[3.1.0]hex-6-ylmethyl]-(3-fluoro-4-morpholin-4-yl-phenyl)-amide |
| 201 | Furan-2-carboxylic acid [3-(4-ethyl-benzyl)-3-aza-bicyclo[3.1.0]hex-6-ylmethyl]-(3-fluoro-4-morpholin-4-yl-phenyl)-amide |
| 202 | N-[3-(4-Ethyl-benzyl)-3-aza-bicyclo[3.1.0]hex-6-ylmethyl]-N-(3-fluoro-4-morpholin-4-yl-phenyl)-2-methyl-benzamide |
| 203 | Benzo[b]thiophene-2-carboxylic acid [3-(4-ethyl-benzyl)-3-aza-bicyclo[3.1.0]hex-6-ylmethyl]-(3-fluoro-4-morpholin-4-yl-phenyl)-amide |
| 204 | 4-Cyano-N-[3-(4-ethyl-benzyl)-3-aza-bicyclo[3.1.0]hex-6-ylmethyl]-N-(3-fluoro-4-morpholin-4-yl-phenyl)-benzamide |
| 205 | 4-Ethyl-N-[3-(4-ethyl-benzyl)-3-aza-bicyclo[3.1.0]hex-6-ylmethyl]-N-(3-fluoro-4-morpholin-4-yl-phenyl)-benzamide |
| 206 | 3-Chloro-thiophene-2-carboxylic acid [3-(4-ethyl-benzyl)-3-aza-bicyclo[3.1.0]hex-6-ylmethyl]-(3-fluoro-4-morpholin-4-yl-phenyl)-amide |
| 207 | N-[3-(4-Ethyl-benzyl)-3-aza-bicyclo[3.1.0]hex-6-ylmethyl]-N-(3-fluoro-4-morpholin-4-yl-phenyl)-2-methylsulfanyl-nicotinamide |
| 208 | 1-Methyl-1H-pyrazole-3-carboxylic acid [3-(4-ethyl-benzyl)-3-aza-bicyclo[3.1.0]hex-6-ylmethyl]-(3-fluoro-4-morpholin-4-yl-phenyl)amide |
| 209 | N-[3-(4-Ethyl-benzyl)-3-aza-bicyclo[3.1.0]hex-6-ylmethyl]-2,4-difluoro-N-(3-fluoro-4-morpholin-4-yl-phenyl)-benzamide |
| 210 | N-[3-(4-Ethyl-benzyl)-3-aza-bicyclo[3.1.0]hex-6-ylmethyl]-N-(3-fluoro-4-morpholin-4-yl-phenyl)-nicotinamide |
| 211 | 3,5-Dimethyl-1H-pyrrole-2-carboxylic acid [3-(4-ethyl-benzyl)-3-aza-bicyclo[3.1.0]hex-6-ylmethyl]-(3-fluoro-4-morpholin-4-yl-phenyl)-amide |
| 212 | 1-Methyl-1H-pyrrole-2-carboxylic acid [3-(4-ethyl-benzyl)-3-aza-bicyclo[3.1.0]hex-6-ylmethyl]-(3-fluoro-4-morpholin-4-yl-phenyl)-amide |
| 213 | 2-Methyl-thiazole-4-carboxylic acid [3-(4-ethyl-benzyl)-3-aza-bicyclo[3.1.0]hex-6-ylmethyl]-(3-fluoro-4-morpholin-4-yl-phenyl)-amide |
| 214 | 4-Bromo-N-[3-(4-ethyl-benzyl)-3-aza-bicyclo[3.1.0]hex-6-ylmethyl]-N-(3-fluoro-4-morpholin-4-yl-phenyl)-benzamide |
| 215 | 5-Oxo-pyrrolidine-2-carboxylic acid [3-(4-ethyl-benzyl)-3-aza-bicyclo[3.1.0]hex-6-ylmethyl]-(3-fluoro-4-morpholin-4-yl-phenyl)-amide |
| 216 | N-[3-(4-Ethyl-benzyl)-3-aza-bicyclo[3.1.0]hex-6-ylmethyl]-N-(3-fluoro-4-morpholin-4-yl-phenyl)-2-(2-methoxy-phenyl)-acetamide |
| 217 | N-[3-(4-Ethyl-benzyl)-3-aza-bicyclo[3.1.0]hex-6-ylmethyl]-N-(3-fluoro-4-morpholin-4-yl-phenyl)-2-(2-fluoro-phenyl)-acetamide |
| 218 | 1-Acetyl-pyrrolidine-2-carboxylic acid [3-(4-ethyl-benzyl)-3-aza-bicyclo[3.1.0]hex-6-ylmethyl]-(3-fluoro-4-morpholin-4-yl-phenyl)-amide |
| 219 | Thiophene-3-carboxylic acid [3-(4-ethyl-benzyl)-3-aza-bicyclo[3.1.0]hex-6-ylmethyl]-(3-fluoro-4-morpholin-4-yl-phenyl)-amide |
| 220 | N-[3-(4-Ethyl-benzyl)-3-aza-bicyclo[3.1.0]hex-6-ylmethyl]-N-(3-fluoro-4-morpholin-4-yl-phenyl)-2-pyridin-3-yl-acetamide |
| 221 | 5-Bromo-thiophene-2-carboxylic acid [3-(4-ethyl-benzyl)-3-aza-bicyclo[3.1.0]hex-6-ylmethyl]-(3-fluoro-4-morpholin-4-yl-phenyl)-amide |
| 222 | N-[3-(4-Ethyl-benzyl)-3-aza-bicyclo[3.1.0]hex-6-ylmethyl]-N-(3-fluoro-4-morpholin-4-yl-phenyl)-2-o-tolyl-acetamide |

Example 5

Thiophene-2-carboxylic acid [3-(4ethyl-benzyl)-3-aza-bicyclo[3.1.0]hex-6-ylmethyl]-[3-fluoro-4-(4-methyl-piperazin-1-yl)-phenyl]-amide To a stirring solution of the (4-Bromo-3-fluoro-phenyl)-[3-(4-ethyl-benzyl)-3-aza-bicyclo[3.1.0]hex-6-ylmethyl]-amine prepared above (100 mg, 0.20 mmol) in 3 mL of anhydrous toluene at room temperature was added N-methylpiperazine (0.03 mL, 0.23 mmol), BINAP (9.1 mg, 0.015 mmol), NaOtBu (26 mg, 0.27 mmol) and palladium (II) acetate (22 mg, 0.009 mmol). The mixture was evacuated under reduced pressure and purged with $N_2$. The reaction mixture was heated to 100° C. for 18 hours. The mixture was cooled to room temperature, quenched with saturated NaHCO$_3$, and extracted with CH$_2$Cl$_2$. The combined organic layers were dried and concentrated under reduced pressure. Purification of the crude material by flash chromatography with 5% MeOH/CH$_2$Cl$_2$ produced the desired product (24 mg) as a white foam. 400 MHz $^1$H NMR (CDCl$_3$) δ 7.27-7.29 (m, 1H), 7.08-7.15 (m, 4H), 6.89-6.98 (m, 3H), 6.77-6.84 (m, 2H), 3.64 (d, J=7.05 Hz, 2H), 3.53 (s, 2H), 3.15-3.17 (m, 4H), 2.90 (brs, 2H), 2.57-2.62 (m, 6H), 2.29-2.40 (m, 5H), 1.39 (brs,1H), 1.27 (brs, 2H), 1.19 (t, 3H); MS (M+1) 533.2.

The following compounds were made using the above procedure of Example 5, starting with the appropriate starting bromide of formula (XV) and the corresponding amine ($R^{16}R^{17}NH$).

Furthermore, pharmaceutically acetable salts of the compounds listed below can be prepared as follows. To a stirring solution of compounds of the general formula (XVI) (prepared as described above in Example 5, 1.0 equiv.) in a suitable solvent such as methyl ethyl ketone, methylene chloride/methanol (1:1) or methanol (0.1 M) at room temperature was added the appropriate acid, such as hydrochloric acid, citric acid, p-toluenesulfonic acid, methansulfonic acid or benzene sulfonic acid (1.0 equiv) in one portion. The resulting mixture was stirred at room temperature for up to 18 hours, during which time a precipitate formed. Filtration of the solid and drying under reduced pressure afforded the desired salts.

Thiophene-2-carboxylic acid [4-(4-acetyl-piperazin-1-yl)-3-fluoro-phenyl]-[3-(4-ethyl-benzyl)-3-aza-bicyclo[3.1.0]hex-6-ylmethyl]-amide 400 MHz $^1$H NMR (CDCl$_3$) δ 7.27-7.29 (m, 1H), 6.95-7.09 (m, 4H), 6.88-6.91 (m, 2H), 6.85-6.87 (m, 2H), 6.78-6.80 (m, 1H), 3.77-3.80 (m, 2H), 3.62-3.66 (m, 4H), 3.50 (brs, 2H), 3.06-3.12 (m, 4H), 2.82-2.88 (m, 2H), 2.59 (q, 2H), 2.29 (brs, 2H), 2.13 (s, 3H), 1.44-1.47 (m, 1H), 1.17-1.25 (m, 5H); MS (M+1) 561.2.

| Compound ID | IUPAC NAME |
| --- | --- |
| 223 | Thiophene-2-carboxylic acid [4-(4-acetyl-[1,4]diazepan-1-yl)-3-Tfluoro-phenyl]-[3-(4-ethyl-benzyl)-3-aza-bicyclo[3.1.0]hex-6-ylmethyl]-amide |

Example 6

Thiophene-2-carboxylic acid [3-(4-tert-butyl-benzoyl)-3-aza-bicyclo[3.1.0]hex-6-ylmethyl]-(3,4,5,6-tetrahydro-2H-[1,2']bipyridinyl-5'-yl)-amide A stirring solution of the Thiophene-2-carboxylic acid [3-(4-tert-butyl-benzoyl)-3-aza-bicyclo[3.1.0]hex-6-ylmethyl]-(6-chloro-pyridin-3-yl)-amide prepared above (50 mg, 0.10 mmol) in 1 mL of anhydrous piperidine was heated to 150° C. for 18 hours. The mixture was cooled to room temperature, quenched with water, and extracted with Et$_2$O. The combined organic layers were dried over anhydrous MgSO$_4$ and concentrated under reduced pressure to yield the desired compound (40 mg, 73%).

The following compounds were made using the above procedure of Example 6, starting with the appropriate starting bromo or chloro compounds of formula (XVII) and the corresponding amine ($R^{16}R^{17}NH$). Furthermore, pharmaceutically acetable salts of the compounds listed below can be prepared as follows. To a stirring solution of compounds of the general formula (XVI) (prepared as described above in Example 6, 1.0 equiv.) in a suitable solvent such as methyl ethyl ketone, methylene chloride/methanol (1:1) or methanol (0.1 M) at room temperature was added the appropriate acid, such as hydrochloric acid, citric acid, p-toluenesulfonic acid, methansulfonic acid or benzene sulfonic acid (1.0 equiv) in one portion. The resulting mixture was stirred at room temperature for up to 18 hours, during which time a precipitate formed. Filtration of the solid and drying under reduced pressure afforded the desired salts.

| Compound ID | IUPAC NAME |
| --- | --- |
| | 3-aza-bicyclo[3.1.0]hex-6-ylmethyl]-amide |
| 224 | Thiophene-2-carboxylic acid [6-(4-acetyl-piperazin-1-yl)-pyridin-3-yl]-[3-(4-tert-butyl-benzoyl)-3-aza-bicyclo[3.1.0]hex-6-ylmethyl]-amide |
| 225 | Thiophene-2-carboxylic acid [3-(4-tert-butyl-benzoyl)-3-aza-bicyclo[3.1.0]hex-6-ylmethyl]-(3,4,5,6-tetrahydro-2H-[1,2']bipyridinyl-5'-yl)-amide |
| 226 | Thiophene-2-carboxylic acid [3-(4-tert-butyl-benzoyl)-3-aza-bicyclo[3.1.0]hex-6-ylmethyl]-[6-(5-methyl-2,5-diaza-bicyclo[2.2.1]hept-2-yl)-pyridin-3-yl]-amide |
| 227 | Thiophene-2-carboxylic acid [3-(4-tert-butyl-benzoyl)-3-aza-bicyclo[3.1.0]hex-6-ylmethyl]-[6-(4-methyl-piperazin-1-yl)-pyridin-3-yl]-amide |
| 228 | Thiophene-2-carboxylic acid [3-(4-tert-butyl-benzoyl)-3-aza-bicyclo[3.1.0]hex-6-ylmethyl]-{6-[ethyl-(2-methoxy-ethyl)-amino]-pyridin-3-yl}-amide |
| 229 | Thiophene-2-carboxylic acid [3-(4-tert-butyl-benzoyl)-3-aza-bicyclo[3.1.0]hex-6-ylmethyl]-{6-[(1H-imidazol-2-ylmethyl)-methyl-amino]-pyridin-3-yl}-amide |
| 230 | Thiophene-2-carboxylic acid [3-(4-tert-butyl-benzoyl)-3-aza-bicyclo[3.1.0]hex-6-ylmethyl]-[6-(3-oxo-piperazin-1-yl)-pyridin-3-yl]-amide |
| 231 | Thiophene-2-carboxylic acid [3-(4-tert-butyl-benzoyl)-3-aza-bicyclo[3.1.0]hex-6-ylmethyl]-{6-[(2-methoxy-ethyl)-methyl-amino]-pyridin-3-yl}-amide |
| 232 | Thiophene-2-carboxylic acid [3-(4-tert-butyl-benzoyl)-3-aza-bicyclo[3.1.0]hex-6-ylmethyl]-[6-(3-dimethylamino-pyrrolidin-1-yl)-pyridin-3-yl]-amide |

-continued

| Compound ID | IUPAC NAME |
|---|---|
| 233 | Thiophene-2-carboxylic acid [3-(4-tert-butyl-benzoyl)-3-aza-bicyclo[3.1.0]hex-6-ylmethyl]-[6-(4-methyl-[1,4]diazepan-1-yl)-pyridin-3-yl]-amide |
| 234 | Thiophene-2-carboxylic acid [3-(4-tert-butyl-benzoyl)-3-aza-bicyclo[3.1.0]hex-6-ylmethyl]-[6-(3-diethylamino-pyrrolidin-1-yl)-pyridin-3-yl]-amide |
| 235 | Thiophene-2-carboxylic acid (6-[1,3']bipyrrolidinyl-1'-yl-pyridin-3-yl)-[3-(4-tert-butyl-benzoyl)-3-aza-bicyclo[3.1.0]hex-6-ylmethyl]-amide |
| 236 | Thiophene-2-carboxylic acid [3-(4-tert-butyl-benzoyl)-3-aza-bicyclo[3.1.0]hex-6-ylmethyl]-[6-(3-morpholin-4-yl-azetidin-1-yl)-pyridin-3-yl]-amide |
| 237 | Thiophene-2-carboxylic acid [3-(4-tert-butyl-benzoyl)-3-aza-bicyclo[3.1.0]hex-6-ylmethyl]-[6-(8-methyl-3,8-diaza-bicyclo[3.2.1]oct-3-yl)-pyridin-3-yl]-amide |
| 238 | Thiophene-2-carboxylic acid [3-(4-tert-butyl-benzoyl)-3-aza-bicyclo[3.1.0]hex-6-ylmethyl]-[6-(3-morpholin-4-yl-pyrrolidin-1-yl)-pyridin-3-yl]-amide |
| 239 | Thiophene-2-carboxylic acid [3-(4-tert-butyl-benzoyl)-3-aza-bicyclo[3.1.0]hex-6-ylmethyl]-[6-(2,3-dihydro-5H-benzo[f][1,4]oxazepin-4-yl)-pyridin-3-yl]-amide |

What is claimed is:

1. A compound of formula I, wherein

Formula I

Y is H or $(R^{100})_k$—$R^1$—$(R^6)_m$;
k is 0 or 1;
l=0, 1, 2 or 3;
m=1, 2 or 3;
n is 0, 1, 2, 3 or 4;
o is 0 or 1;
p is 0, 1, 2, or 3;
q is 0, 1, 2, 3 or 4;
r is 1 or 2;
s is 0, 1, 2, 3 or 4;
t is 0 or 1;
u is 1, 2, or 3;
v is 1, 2, or 3;
$R^{100}$ is —$CH_2$—, —$CH(C_1\text{-}C_3)$alkyl-, —C(=O)— or —$SO_2$—;
$R^1$ is —$(C_1\text{-}C_6)$alkyl, —$(C_3\text{-}C_8)$cycloalkyl, -(4 to 7 membered) heterocycloalkyl, —$(CH_2)_r$—$(C_6\text{-}C_{10}$ aryl) or -(5 to 10 membered) heteroaryl, or -(5 to 10 membered) tetrahydro-heteroaryl;
each $R^6$ can be same or different and is independently selected from H, halo, —$(C_1\text{-}C_6)$alkyl-B, $(C_1\text{-}C_7)$alkoxy-D, $(C_2\text{-}C_4)$alkenoxy, $(C_1\text{-}C_6)$alkyl-OH, —OH, CN, —$NO_2$, —$CR^7R^8R^9$, —$NR^{20}R^{21}$, —NHCOalkyl$(C_1\text{-}C_3)$, NHSO$_2$alkyl$(C_1\text{-}C_3)$, C(=O)OR$^{22}$, —$R^{23}$—C(=O)OR$^{22}$, —C(=O)NH$_2$, phenyl-E, phenoxy-F, morpholine, —$NR^{20}R^{21}$, aryl, heteroaryl, —S—$R^{24}$, and —$SO_2$—$R^{25}$;
B and D are each independently H, OH, phenyl, diphenyl or trifluro;
E and F are each independently H, alkyl, or halo;
$R^7$, $R^8$ and $R^9$ are each independently H, $(C_1\text{-}C_4)$ alkyl, —OH, —O—$(C_1\text{-}C_4)$alkyl, —CN, —$NR^{26}R^{27}$ and —NHC(=O) $(C_1\text{-}C_3)$alkyl, wherein said alkyl groups are optionally substituted with OH, OCH$_3$, NH$_2$, NHC(=O) $(C_1\text{-}C_3)$alkyl, or $R^7$ and $R^8$ together with the carbon atom to which they are attached optionally form a $(C_3\text{-}C_7)$cycloalkyl ring, or a $(C_4\text{-}C_7)$heterocycloalkyl ring which contains 1-3 heteroatoms selected from N, O, S and optionally contains a C=O group;
$R^{20}$ and $R^{21}$ are each independently H or $(C_1\text{-}C_6)$ alkyl;
or $R^{20}$ and $R^{21}$ can be connected by 4 to 7 carbon atoms wherein from one to three of said carbon atoms can optionally be replaced with O, N or S, to form a heterocycloalkyl ring;
or $R^{20}$ and $R^{21}$ can be connected by 3 to 7 atoms selected from C, N, O or S to form a 5 to 10 membered heteroaryl ring;
$R^{22}$, $R^{23}$ and $R^{24}$ are each independently H, or $(C_1\text{-}C_5)$ alkyl;
$R^{25}$ is $(C_1\text{-}C_5)$alkyl;
$R^{26}$ and $R^{27}$ are each independently H or $(C_1\text{-}C_3)$alkyl;
or $R^{26}$ and $R^{27}$ can be connected by 4 to 7 carbon atoms to form a heterocycloalkyl ring;
$R^2$ and $R^3$ are each independently H or $(C_1\text{-}C_3)$alkyl;
$R^4$ and $R^5$ are each independently H or $(C_1\text{-}C_3)$ alkyl;
or $R^4$ and $R^5$ can be taken together form a double bond to an oxygen to form (C=O), or $R^4$ and $R^5$ are connected with 2 to 4 carbon atoms to form a 3-5 member carbocyclic ring;
A is H or $(C_1\text{-}C_3)$alkyl-$(R^{28})_n$;
$R^{28}$ is independently $(C_1\text{-}C_3)$alkoxy, —OH, —$NR^{12}R^{13}$ or —NHC(=O)$(C_1\text{-}C_4)$alkyl;
$R^{12}$ and $R^{13}$ are each independently H or —$(C_1\text{-}C_4)$alkyl; or
$R^{12}$ and $R^{13}$ can be connected by 4 to 7 carbon atoms to form a heterocycloalkyl ring;
X is a bond, —$CH_2$—$(R^{29})_p$, —C(=O) or —$SO_2$;
$R^{29}$ is —$(C_1\text{-}C_3)$alkyl;

W is alkyl, —($C_3$-$C_8$) cycloalkyl, -(3 to 7 membered) heterocyclcoalkyl, -(3 to 7 membered) heterocyclcoalkyl with 1 or 2 C=O groups, phenyl, or -(5 to 7 member) heteroaryl or heterocyclic;

$R^{30}$ is —($C_1$-$C_4$)alkyl, —($C_1$-$C_3$)alkoxy, CN, —F, —Cl, —Br, —I, —$NR^{18}R^{19}$, —NHC(=O)$R^{18}$, —$SCH_3$ or —C(=O)$CH_3$;

$R^{18}$ and $R^{19}$ are each independently H or —($C_1$-$C_3$)alkyl;

Q is a bond, —CH—($R^{31}$)$_r$, —C(=O) or —$SO_2$;

$R^{31}$ is independently H or —($C_1$-$C_3$)alkyl;

Z is phenyl;

$R^{14}$ is F, Cl, Br, I, V, H, —$NR^{16}R^{17}$, —$OR^{16}$, —C(=O)$NR^{16}R^{17}$, —($SO_2$)$NR^{16}R^{17}$, or —$NR^{32}$—C=O—$R^{33}$, $R^{15}$ is —($C_1$-$C_3$)alkyl, —($C_1$-$C_3$)alkoxy, —F, —Br, —Cl, —I —OH or —CN;

V is —($C_3$-$C_8$)cycloalkyl, —($C_1$-$C_5$)alkyl, (5 to 7 membered) heterocycloalkyl, (5 to 7 membered)heterocycloalkyl substituted with 1 or 2 C=O groups or 1, 2, or 3 ($C_1$-$C_5$)alkyl groups;

$R^{16}$ and $R^{17}$ are each independently H, —($C_1$-$C_6$)alkyl-($R^{34}$)$_u$, or ($C_3$-$C_8$)cycloalkyl-($R^{35}$)$_v$;

or $R^{16}$ and $R^{17}$ together with the nitrogen atom to which they are attached form a 4 to 7 membered heterocycloalkyl ring optionally containing from 1 to 3 additional heteroatoms independently selected from N, S and O, and contain C=O, wherein said heterocycloalkyl ring is optionally and independently substituted with 1 to 3 substituents independently selected from ($C_1$-$C_4$) alkyl, OH, ($C_1$-$C_4$)alkoxy, $NH_2$, —NH(C=O)alkyl, —N($C_1$-$C_3$)alkyl)$_2$, —C(=O)$CH_3$, $CONH_2$, $CO_2H$, $CH_2OH$, $CH_2$Oalkyl($C_2$-$C_4$), and (5 to 7 membered) heterocycloalkyl;

$R^{32}$ and $R^{33}$ are each independently H or ($C_1$-$C_5$)alkyl;

or $R^{32}$ and $R^{33}$ can be taken together to form a 3-7 membered cycloalky ring, a 3-7 membered heterocycloalkyl ring with 1 to 3 heteroatoms, or a 5-7 membered heteroaryl ring with 1 to 3 heteroatoms;

$R^{34}$ and $R^{35}$ are each independently H, OH, ($C_1$-$C_5$)alkyl, ($C_2$-$C_4$)alkoxy, $NH_2$, NH(C=O)($C_1$-$C_3$)alkyl, or a 5 to 7 membered heterocycloalkyl;

or $R^{34}$ and $R^{35}$ can be taken together to form a bridge containing 1-2 carbon atoms;

or pharmaceutically acceptable salts thereof.

2. A compound as in claim 1, wherein the stereochemistry is as in formula II

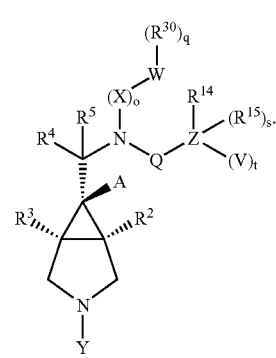

Formula II

3. A compound as in claim 1, wherein the stereochemistry is as in formula III

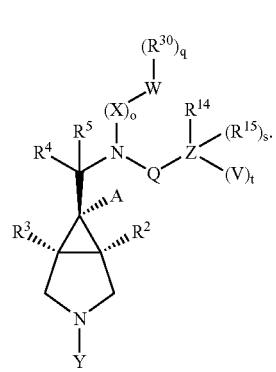

Formula III

4. A pharmaceutical composition comprising a compound of claim 1, or a pharmaceutically acceptable salt thereof, and a pharmaceutically acceptable carriers.

* * * * *